US012746066B2

(12) United States Patent
Charest et al.

(10) Patent No.: US 12,746,066 B2
(45) Date of Patent: Sep. 29, 2026

(54) SYSTEMS AND METHODS FOR A SPINAL ANATOMY REGISTRATION FRAMEWORK

(71) Applicant: KATO Medical, Inc., Carlsbad, CA (US)

(72) Inventors: Joshua Charest, San Diego, CA (US); Albert Hill, Carlsbad, CA (US)

(73) Assignee: KATO Medical, Inc., Carlsbad, CA (US)

( * ) Notice: Subject to any disclaimer, the term of this patent is extended or adjusted under 35 U.S.C. 154(b) by 0 days.

(21) Appl. No.: 18/392,384

(22) Filed: Dec. 21, 2023

(65) Prior Publication Data

US 2024/0206973 A1 Jun. 27, 2024

Related U.S. Application Data

(60) Provisional application No. 63/434,295, filed on Dec. 21, 2022.

(51) Int. Cl.

| | |
|---|---|
| ***A61B 34/10*** | (2016.01) |
| ***A61B 17/70*** | (2006.01) |
| ***A61B 17/86*** | (2006.01) |
| ***A61B 17/88*** | (2006.01) |
| ***A61B 34/00*** | (2016.01) |
| ***A61B 34/30*** | (2016.01) |
| ***A61B 90/00*** | (2016.01) |

(52) U.S. Cl.
CPC .......... *A61B 34/10* (2016.02); *A61B 17/7082* (2013.01); *A61B 17/86* (2013.01); *A61B 17/8875* (2013.01); *A61B 34/25* (2016.02); *A61B 34/30* (2016.02); *A61B 90/06* (2016.02); *A61B 2034/107* (2016.02); *A61B 2090/066* (2016.02)

(58) Field of Classification Search
CPC ......... A61B 34/10; A61B 34/25; A61B 34/32; A61B 17/70; A61B 17/7082; A61B 17/86; A61B 17/88; A61B 17/8875; A61B 90/06
See application file for complete search history.

(56) References Cited

U.S. PATENT DOCUMENTS

| | | | | |
|---|---|---|---|---|
| 10,149,732 | B2 | 12/2018 | Overmyer et al. | |
| 2018/0132955 | A1 | 5/2018 | Kapadia et al. | |
| 2019/0328461 | A1 | 10/2019 | Kemp et al. | |
| 2020/0390362 | A1 | 12/2020 | Westerhof et al. | |
| 2022/0039875 | A1 | 2/2022 | Choi et al. | |
| 2022/0160428 | A1 * | 5/2022 | Murray .................. | G16H 40/63 |
| 2022/0257320 | A1 * | 8/2022 | Junio ..................... | G16H 10/60 |

* cited by examiner

*Primary Examiner* — Christopher J Beccia
(74) *Attorney, Agent, or Firm* — Greenberg Traurig, LLP

(57) ABSTRACT

Disclosed are systems and methods that provide a computerized framework for performing a decision intelligence (DI)-based assessment and/or operation of/on a patient's spine. The disclosed spinal assessment framework provides a robotically actuated screw placement and assessment system. The disclosed framework can be implemented for the performance of a preoperative, intra-operative and/or post-operative spinal assessment/procedure. The disclosed spinal framework can be utilized for robotically-actuated pedicle screw placement, robotically-actuated bone removal and/or spine construct optimization via a spinal flexibility and alignment assessment.

12 Claims, 27 Drawing Sheets

| Programming Logic | Lateral Shot |
|---|---|
| 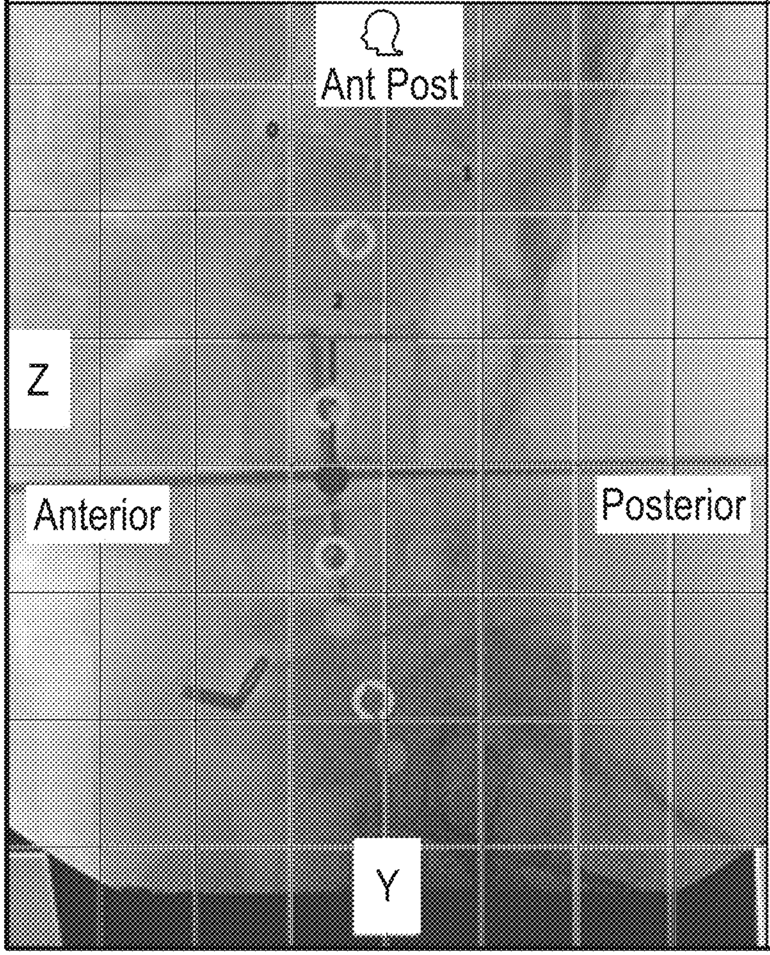 | **Sagittal Plane** - Coordinate space (Y,Z)<br><br>**User-generated Solid Lines** - drawn from anterior aspect of superior endplate to posterior aspect of superior endplate<br><br>**Perpendicular Dotted Lines** - user identifies intersection of perpendicular line originating at midpoint of user-generated solid line line with inferior endplate<br><br>**Centroid YZ** = midpoint of perpendicular line<br><br>**Ferguson Angle** = tan-1 ((Z(0)-Z(1))/Y(0)-Y(1)) |

FIG. 4B

| Programming Logic | Anterior-Posterior (AP) Shot |
|---|---|
| 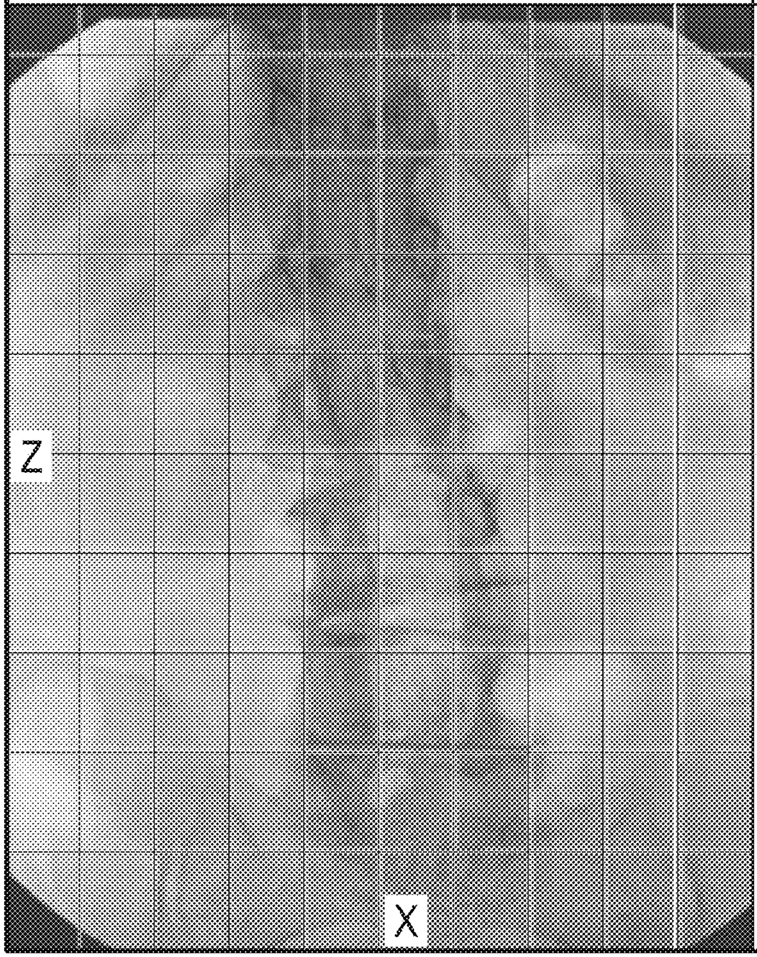 | **Frontal plane** - Coordinate space (X,Z)<br><br>**User-generated Solid Lines** - drawn from patient's left aspect of superior endplate to patient's right aspect of superior endplate<br><br>**Perpendicular Dotted Lines** - line drawn from midpoint of user-generated line with height defined by Z on lateral shot<br><br>**Centroid (Z,X)** = midpoint of perpendicular line<br><br>**Wag Angle** = tan-1 ((Z(0)-Z(1))/X(0)-X(1)) |

FIG. 4C

SYSTEMS AND METHODS FOR A SPINAL ANATOMY REGISTRATION FRAMEWORK

CROSS-REFERENCE TO RELATED APPLICATIONS

This application claims the benefit of priority from U.S. Provisional Patent Application No. 63/434,295, filed on Dec. 21, 2022, whereby the contents of which are incorporated herein in their entirety by reference.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present disclosure is generally related to a preoperative, intra-operative and/or post-operative spinal assessment, and more particularly, to a computerized framework for performing a decision intelligence (DI)-based assessment and/or operation of a patient's spine.

BACKGROUND

Currently, there exist many different types of spinal surgeries. For example, a patient may require spinal fusion, microdiscectomy, artificial disc replacement, laminectomy, vertebroplasty, foraminotomy, interlaminar implants, and the like.

Typically, a single spine surgeon is used to perform such procedures. However, under complex situations, an additional spine surgeon may be required. In most cases, having dual spine surgeons versus a single spine surgeon has evidenced less blood loss (e.g., 763 ml versus 1524 ml, for example), few blood transfusions (e.g. 0.5 versus 2.3). and fewer 90-day readmissions (0% versus 15.8%), and the like.

However, procedures requiring pedicle screws (e.g., spinal fusion, for example) and osteotomies, under conventional surgical methodologies and technologies, despite a dual surgeon set-up, have realized multiple problems/setbacks. For example, pedicle screws can be malpositioned, which can require a revision procedure and/or lead to a malpractice lawsuit. Indeed, of the 400 k+ lumbar fusion procedures performed within a past year in the United States, 1.5% involved a malpositioned pedicle screw.

SUMMARY

To address these concerns and problems in the medical fields, convention involves utilizing robots; however, many conventional robots have limited capabilities and/or functionality. For example, many current robots are limited in the mechanism that are utilized for screw placement, which they do not perform at an accuracy level that eliminates chances of a required revision procedure. For example, many current robots leverage a node geometry associated with a predetermined path, whereby a screw can be rotated a certain number of times. However, this does not take into account the rate of insertion, driving force and/or variations caused by both, inter alia, which when not accounted for, among other variables, can lead to a malpositioned screw. Moreover, current robots may have driving forces across multiple axes, which can lead to improper positioning and/or insertion into a patient's spine (e.g., cause the robotic tool to unintentionally shift position and/or angle thereby leading to an improper instrumentation of the pedicle screw).

Additionally, current applied robotics in the spinal medical arts require the surgeon to effectively become a robotics expert. That is, rather than simply focusing on patient care and the procedure at hand, the spine surgeon must often now become a robotics technician to troubleshoot the robot that the surgeon is supposed to be relying on.

Thus, according to some embodiments, the disclosed systems and methods provide a novel spinal assessment framework that addresses the shortcomings in the art, inter alia, by providing a robotically actuated screw placement and assessment system. As discussed herein, according to some embodiments, the disclosed framework can be implemented for the performance of a preoperative, intra-operative and/or post-operative spinal assessment/procedure. In some embodiments, the spinal framework discussed herein can be utilized for robotically-actuated pedicle screw placement, robotically-actuated bone removal and/or a spinal flexibility and alignment assessment.

According to some embodiments, the framework can effectuate a variety of specifically configured methodologies to ensure improved efficiency, accuracy and safety of spinal procedures as compared to existing mechanisms. According to some embodiments, the disclosed framework can perform and/or enable execution of an intra-operative registration of a patient's spinal anatomy to a navigation space during spinal surgery. According to some embodiments, as discussed in more detail below, the disclosed framework can utilize various sensors and/or detectors to determine the pose estimation of a spinal anatomy in a navigation space. In some embodiments, the framework can invalidate a previously assumed pose estimation of a spinal anatomy in a navigation space during a spine surgery, as discussed in more detail below.

According to some embodiments, the disclosed framework can be configured for, and execute mechanisms for determining an anatomical system and/or the anatomical system's accuracy. In some embodiments, as discussed below, the framework can perform a determination as to an accuracy of an anatomical system from multiple mechanical touchpoints on a patient bone/anatomy.

According to some embodiments, the disclosed framework can be configured for, and execute mechanisms for a placement of a pedicle screw(s) autonomously via robotics. In some embodiments, as discussed below, the framework can determine and/or leverage a screw trajectory, skive likelihood (or probability), optimal pilot hole size, and the like, and implement a robot (e.g., a 2-armed robot, for example) to implant the pedicle screw.

According to some embodiments, the disclosed framework can be configured for, and execute mechanisms for implementation of a linear actuator end effector. In some embodiments, as discussed below, the framework can effectuate placement of pedicle screws via the linear actuator end effector, which can improve workflow efficiency and safety (e.g., by decreasing a number and range of robotic movements and steps compared to conventional robots/robotics).

According to some embodiments, the disclosed framework can be configured for, and execute mechanisms for determining a tracking array shift from a camera element. In some embodiments, as discussed below, the framework can determine a gross patient tracking array movement based on camera-centric tracking. In some embodiments, the framework can perform a re-registration of a patient tracking array after the gross movement determination, as discussed in more detail below.

According to some embodiments, the disclosed framework can be configured for, and execute mechanisms for avoiding a line of sight obstruction during a spinal procedure (e.g., pedicle screw insertion/placement). In some embodiments, as discussed in more detail below, the framework can operate to determine an optimal camera placement for simultaneously viewing a dynamic reference base (DRB) and an instrument tracking array, which can be based on a pre-operative planned screw trajectory and/or intra-operative registration. When used herein, the term "optimal" and similar adjectives include both absolutely optimal solutions as well as those that provide results within five percent of absolutely optimal solutions.

Accordingly, according to some embodiments, the disclosed framework can be configured to execute, and can operate to perform each of the disclosed embodiments as part of an overall preoperative, intra-operative and/or post-operative procedure, whereby the analysis performed pre-operatively can be leveraged during intra-operative and post-operative, as discussed herein.

As such, according to some embodiments, the framework's control of a surgical robot (e.g., FIG. 9A, for example) can realize a optimization of spinal alignment that relies on optimization of pedicle screw fixation (e.g., screw accuracy) and optimization of spinal flexibility (e.g., planning). Accordingly, there are no validated or known methods that currently exist that determine the initial fixation strength of a pedicle screw, as provided for herein, whereby for the first time, a surgeon's "feel" can be quantified, which can lead to smarter intra-operative decisions that can be made regarding cement augmentation, interbody placement and osteotomy.

According to some embodiments, methods are disclosed for performing a DI-based assessment and/or operation of/on a patient's spine. In accordance with some embodiments, the present disclosure provides a non-transitory computer-readable storage medium for carrying out the above-mentioned technical steps of the framework's functionality. The non-transitory computer-readable storage medium has tangibly stored thereon, or tangibly encoded thereon, computer readable instructions that when executed by a device cause at least one processor to perform methods for performing a DI-based assessment and/or operation of/on a patient's spine.

In accordance with one or more embodiments, an apparatus and/or system is provided that includes one or more processors and/or computing devices configured to provide functionality in accordance with such embodiments. In accordance with one or more embodiments, functionality is embodied in steps of a method performed by at least one computing device. In accordance with one or more embodiments, program code (or program logic) executed by a processor(s) of a computing device to implement functionality in accordance with one or more such embodiments is embodied in, by and/or on a non-transitory computer-readable medium.

DESCRIPTIONS OF THE DRAWINGS

The features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure. In the drawings:

FIGS. 4A-4H depict non-limiting example embodiments for implementing the disclosed systems and methods according to some embodiments of the present disclosure;

DETAILED DESCRIPTION

Figure 1:
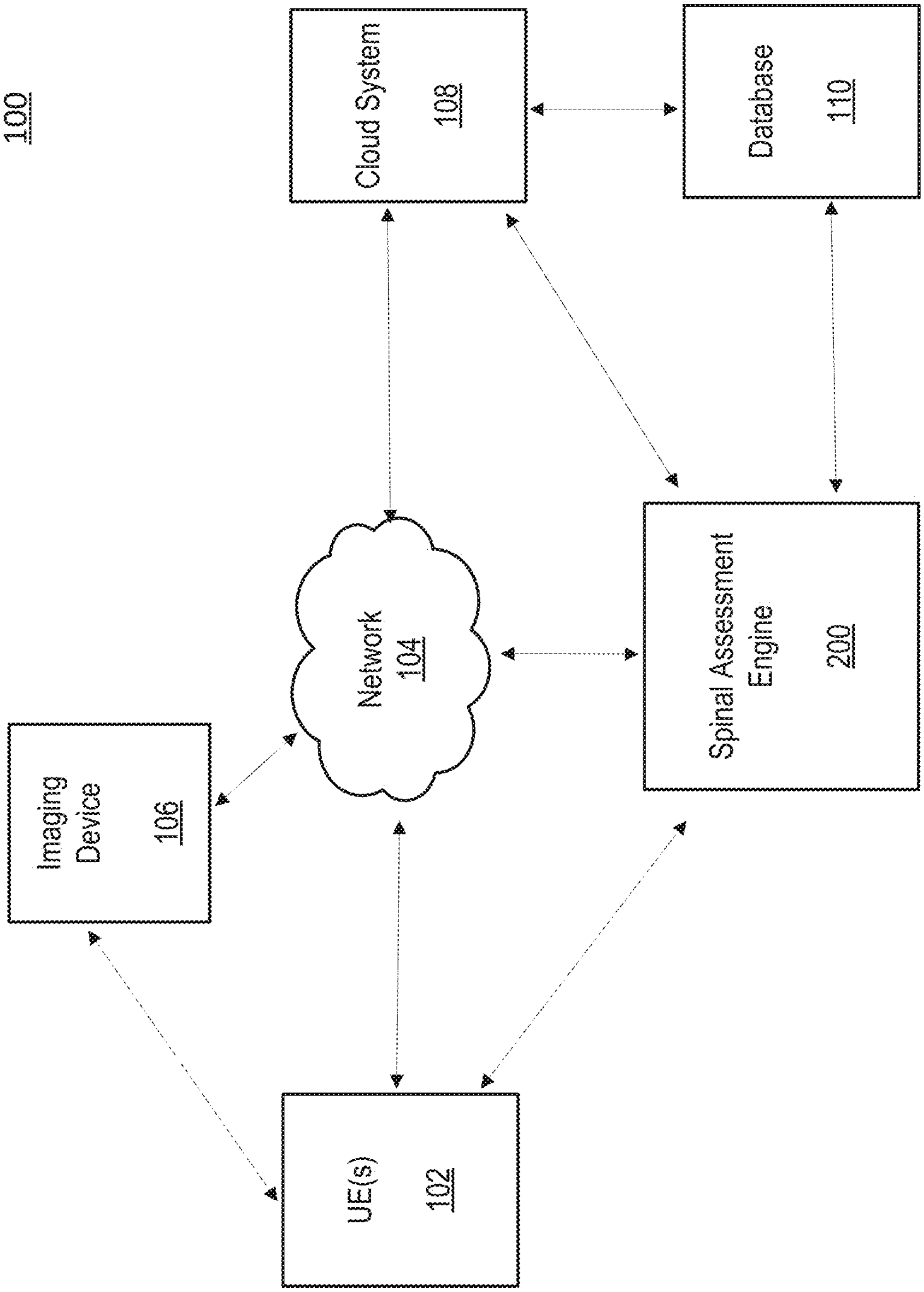
FIG. 1 is a block diagram of an example configuration within which the systems and methods disclosed herein could be implemented according to some embodiments of the present disclosure.

The present disclosure will now be described more fully hereinafter with reference to the accompanying drawings, which form a part hereof, and which show, by way of non-limiting illustration, certain example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and,"

"or," or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure is described below with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

For the purposes of this disclosure a non-transitory computer readable medium (or computer-readable storage medium/media) stores computer data, which data can include computer program code (or computer-executable instructions) that is executable by a computer, in machine readable form. By way of example, and not limitation, a computer readable medium may include computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, optical storage, cloud storage, magnetic storage devices, or any other physical or material medium which can be used to tangibly store the desired information or data or instructions and which can be accessed by a computer or processor.

For the purposes of this disclosure the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

For the purposes of this disclosure a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), a content delivery network (CDN) or other forms of computer or machine-readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further employ a plurality of network access technologies, including Wi-Fi, Long Term Evolution (LTE), WLAN, Wireless Router mesh, or 2nd, 3rd, $4^{th}$ or $5^{th}$ generation (2G, 3G, 4G or 5G) cellular technology, mobile edge computing (MEC), Bluetooth, 802.11b/g/n, or the like. Network access technologies may enable wide area coverage for devices, such as client devices with varying degrees of mobility, for example.

In short, a wireless network may include virtually any type of wireless communication mechanism by which signals may be communicated between devices, such as a client device or a computing device, between or within a network, or the like.

Certain embodiments will be described in greater detail with reference to the figures. For purposes of this disclosure, one of ordinary skill in the art would understand that while the instant disclosure will focus on the spine as a whole, it should not be construed as limiting, as, evidenced from the discussion herein, the disclosed systems and methods can be effectuated and/or implemented according to specific spinal sections or portions, including, but not limited to, vertebrae, disks, cervical spine, thoracic spine, lumbar spine, sacral spine, and the like, or some combination thereof, without departing from the scope of the instant disclosure.

With reference to FIG. 1, system 100 is depicted, which provides functionality for providing a robotically actuated screw placement and assessment system, as discussed herein. According to some embodiments, system 100 can include, but is not limited to, user equipment (UE) 102, network 104, imaging device 106, cloud system 108 and spinal assessment engine 200. It should be understood that while system 100 is depicted as including such components, it should not be construed as limiting, as one of ordinary skill in the art would readily understand that varying numbers of UEs, imaging devices, cloud systems, databases and networks can be utilized; however, for purposes of explanation, system 100 is discussed in relation to the example depiction in FIG. 1.

According to some embodiments, UE 102 can be any type of electronic device that can be used to perform, be part of, relied on, and/or support a spinal procedure. In some embodiments, UE 102 can be, but is not limited to, a mobile phone, tablet, laptop, Internet of Things (IoT) device, wearable device, surgical robot, autonomous machine, and any other type of modern device. According to some embodiments, a non-limiting example of UE 102 is a robotic computer connected to network 104 that can analyze medical images captured by imaging device 106 and utilize them to execute implantation of a pedicle screw into a patient's spine, as discussed herein.

According to some embodiments, non-limiting example embodiments of UE 102 are provided below in reference to FIGS. 9A, 11A-11E and/or 14.

According to some embodiments, imaging device 106 refers to a device used to acquire medical imagery. For example, imaging device 106 can effectuate image capture by any type of known or to be known mechanisms, such as, but not limited to, magnetic resonance imaging (MRI), computerized tomography (CT), X-ray, positron emission tomography (PET), ultrasound arthrography, angiography, fluoroscopy, myelography, and the like. Imaging device 106 may acquire images in real-time and/or be used to create composite images or models, which can also occur in real-time or near-real-time (substantially similar).

According to some embodiments, an imaging device 106 may include any device capable of detecting sound or electromagnetic waves and assembling a visual representation of the detected waves. Imaging device 106 may collect waves from any part of the electromagnetic spectrum or sounds at any range of frequencies, often as a matrix of independently acquired measurements which each representing a pixel of three-dimensional (3D) image. These measurements may be taken simultaneously or in series via a scanning process or a combination of methods. Some pixels of an image produced by an imaging device 106 may be interpolated from direct measurements representing adjacent pixels in order to increase the resolution of a generated image.

In some embodiments, an imaging device(s) 106 may include, correspond to and/or be related to, but not limited to, medical imaging equipment such as, but not limited to, MRI, CT, ultrasound, and the like. Thus, imaging device 106 can be any type of device that produces images, such as any of various machines, for example an MRI machine, compressed sensing (CS) technology, CT scanner, X-ray machine, and the like which is used to produce diagnostic images of a patient's body.

In some embodiments, imaging device 106 may receive or generate imaging data from a plurality of imaging devices 106. For example, in some embodiments, imaging device 106 may include cameras mounted to the ceiling or other structure above the surgical theater, cameras that may be mounted on a tripod or other independent mounting device, cameras that may be body worn by the surgeon or other surgical staff, cameras that may be incorporated into a wearable device (e.g., UE 102), such as an augmented reality device like Google® Glass, Microsoft® HoloLens, and the like, cameras that may be integrated into an endoscopic, microscopic, laparoscopic, or any camera or other imaging device 106 (e.g. ultrasound) that may be present in the surgical theater.

According to some embodiments, imaging device 106 may include and/or execute any type of known or to be known ML and/or AI algorithm and/or software module capable of determining qualitative or quantitative data from medical images, which may be, for example, a deep learning algorithm that has been trained on a data set of medical images.

According to some embodiments, imaging device 106 may be connected to UE 102 and/or configured to electronically communicate with UE 102. In some embodiments, imaging device 106 (and/or UE 102) can include an inertial measurement unit (IMU), which is an electronic device that measures and reports a body's specific force, angular rate and orientation of movement, among other variables. Thus, as discussed below, the IMU executing in association with devices 102 and/or 106 can be utilized to track the movements of the devices 102/106.

Network 104 can be any type of network, such as, but not limited to, a wireless network, cellular network, the Internet, and the like. Network 104 facilitates connectivity of the components of system 100, as illustrated in FIG. 1.

Cloud system 108 can provide for a distributed network of computers including servers and databases. In some embodiments, cloud system 108 can be any type of cloud operating platform and/or network based system upon which applications, operations, and/or other forms of network resources can be located. For example, system 108 can be a service provider and/or network provider from where applications can be accessed, sourced or executed from. In some embodiments, cloud system 108 can include a server(s) and/or a database(s) of information which is accessible over network 104. In some embodiments, a database(s) of cloud system 108 can store a dataset of data and metadata associated with local and/or network information related to a patient, a user(s) of UE 102 and the UE 102, imaging device 106, and the services, applications, content rendered and/or executed by UE 102 and imaging device 106.

In some embodiments, cloud system 108 may be a private cloud and/or network, where access is restricted by isolating the network such as preventing external access, or by using encryption to limit access to only authorized users. For example, a secured, local network associated with a hospital. In some embodiments, cloud system 108 may be a public cloud 108 where access is widely available via the internet.

Spinal assessment engine 200 (referred to as assessment engine 200 and engine 200, interchangeably) includes components for executing a robotically actuated screw placement and assessment system, as discussed in more detail below with respect to at least FIGS. 3-13. According to some embodiments, spinal assessment engine 200 can be a special purpose machine or processor and could be hosted by UE 102. In some embodiments, engine 200 can be hosted by a peripheral device connected to UE 102, imaging device 106 and/or any other device connected to and/or residing on network 104.

In some embodiments, for example, UE 102 may be a computer that is connected to another UE 102, for example, a surgical robot (e.g., FIG. 9A, for example), whereby movements, maneuvers and/or procedures executed by the robot are dictated by the computer.

According to some embodiments, as discussed above, assessment engine 200 can function as an application installed on UE 102, via cloud system 108 and/or imaging device 106. In some embodiments, such application can be a web-based application accessed by UE 102 over network 104 from cloud system 108 (e.g., as indicated by the connection between network 104 and engine 200, and/or the dashed line between UE 102 and engine 200 in FIG. 1). In some embodiments, engine 200 can be configured and/or installed as an augmenting script, program or application (e.g., a plug-in or extension) to another application or program executing on UE 102, via cloud system 108 and/or imaging device 106.

Figure 2:
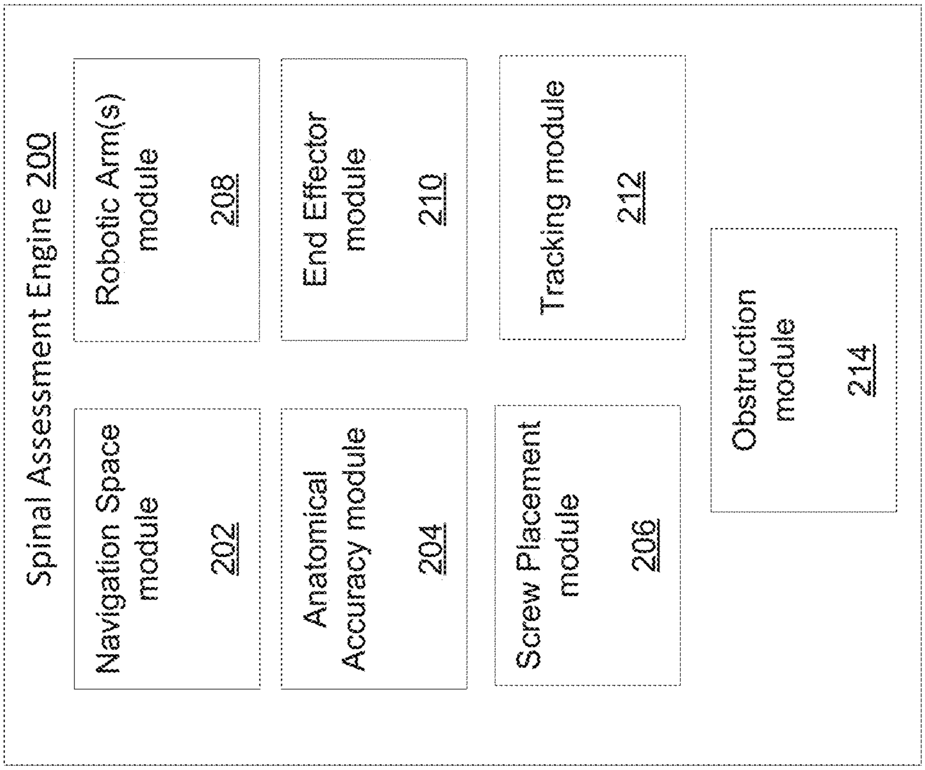
FIG. 2 is a block diagram illustrating components of an exemplary system according to some embodiments of the present disclosure.

As illustrated in FIG. 2, according to some embodiments, assessment engine 200 includes navigation space module 202, anatomical accuracy module 204, screw placement module 206, robotic arm(s) module 208, end effector module 210, tracking module 214 and obstruction module 214.

Figure 3:
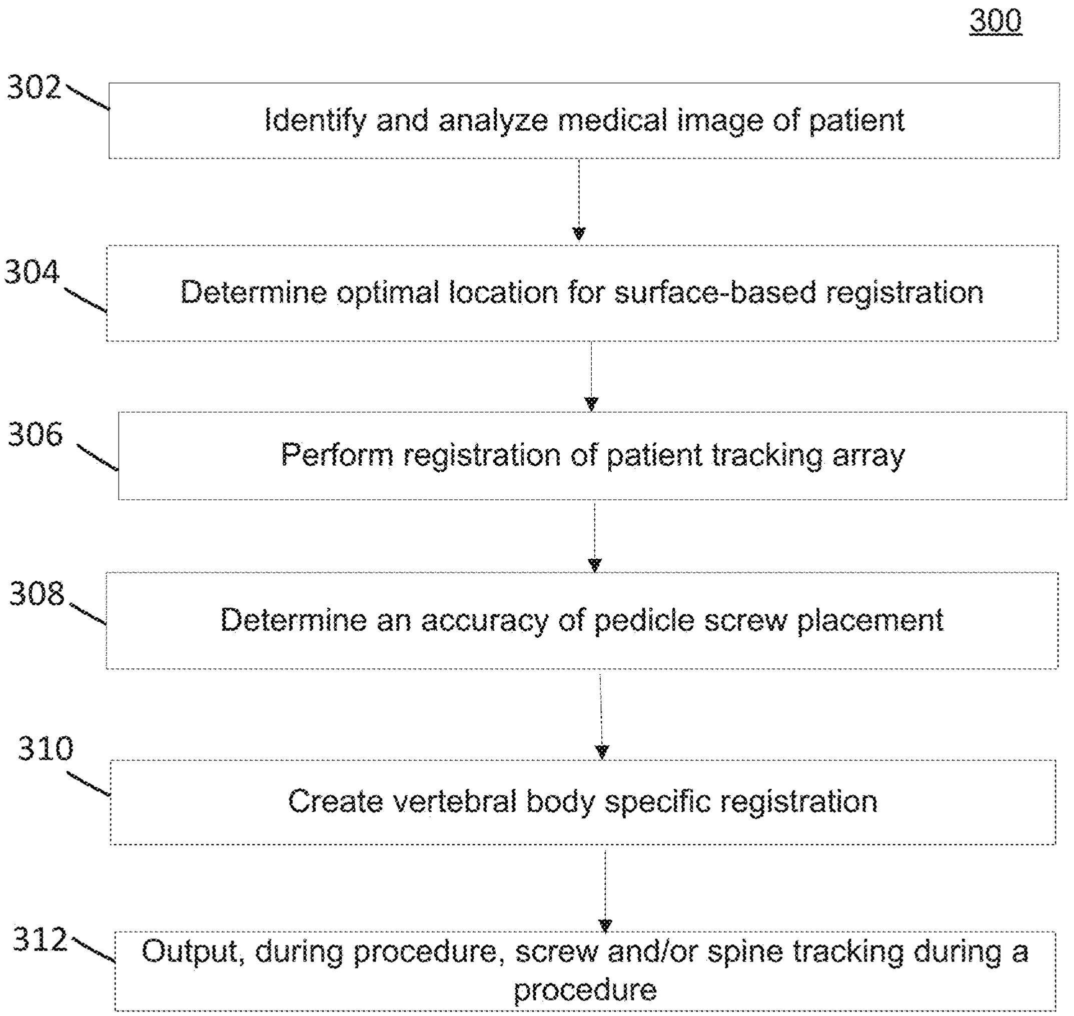
FIG. 3 illustrates an exemplary data flow according to some embodiments of the present disclosure.

According to some embodiments, navigation space module 202 can be configured to execute and/or perform the steps of Process 300 in FIG. 3, discussed infra. In some embodiments, anatomical accuracy module 204 can be configured to execute and/or perform the steps of Process 500 in FIG. 5, discussed infra. In some embodiments, screw placement module 206 can be configured to execute and/or perform the steps of Process 700 in FIG. 7, discussed infra. In some embodiments, robotic arm(s) module 208 can be configured to execute and/or perform the steps of Process 800 in FIG. 8, discussed infra. In some embodiments, end effector module 210 can be configured to execute and/or perform the steps of Process 1000 in FIG. 10, discussed infra. In some embodiments, tracking module 214 can be configured to execute and/or perform the steps of Process 1200 in FIG. 12, discussed infra. And, in some embodiments, obstruction module 214 can be configured to execute and/or perform the steps of Process 1300 in FIG. 13, discussed infra.

According to some embodiments, it should be understood that the engine(s) and modules discussed herein are non-exhaustive, as additional or fewer engines and/or modules (or sub-modules) may be applicable to the embodiments of the systems and methods discussed.

As depicted in FIG. 1, assessment engine 200 and/or cloud system 108 can be associated with a database 110. According to some embodiments, database 110, which can be a patient database, for example, can include data and/or metadata related to a plurality of patients, locations (e.g., hospitals), doctors, practice areas and the like, or some combination thereof, where the data/metadata is stored as an electronic health record (EHR).

According to some embodiments, an EHR refers to a digital record of a patient's health information, which may be collected and stored systematically over time. According to some embodiments, EHR for a patient can be an all-inclusive patient record and can include, but is not limited to, patient identifying information, captured imagery of the patient, demographics, medical history, history of present illness (HPI), progress notes, problems, medications, vital signs, immunizations, laboratory data, and radiology reports. In some embodiments, computer software is used to capture, store, and share patient data in a structured way. The EHR may be created and managed by authorized providers and can make health information instantly accessible to authorized providers across practices and health organizations—such as laboratories, specialists, medical professionals, medical imaging facilities, pharmacies, emergency facilities, and the like. Accordingly, EHRs can be utilized via the disclosed framework, discussed herein.

In some embodiments, database 110 can be included within the functionality of engine 200. That is, for example, engine 200 can include a memory or memory stack that enables data structures associated with database 110 to be hosted and/or remotely identified via a set of pointers or resource identifiers (uniform resource identifiers (URIs), for example). In some embodiments, database 110 can be located on a network location, and accessible to engine 200—for example, in some embodiments, database 110 can be associated with cloud system 108. In some embodiments, database 110 can be configured as a look-up table (LUT), blockchain (e.g., distributed ledger) and/or any other type of secure data repository.

More detail of the operations, configurations and functionalities of engine 200 and each of its modules, and their role within embodiments of the present disclosure will be discussed below.

FIG. 3 provides Process 300 which details embodiments for performing an intra-operative registration of spinal anatomy to navigation space during spinal surgery.

According to some embodiments, as discussed herein, engine 200 can execute Process 300 via a system configuration (e.g., as provided in FIG. 1), where UE 102 can be configured with a navigational instrument and transducer. For example, UE 102 can be provided as the surgical robot provided in FIG. 9A, as discussed in more detail below. In some embodiments, UE 102 can determine a surface topography of an object it is contacting and leverage a transducer to communicate the captured data to an external computer processor (e.g., another UE 102). According to some embodiments, the processing by UE 102 that is contact with the object utilizing a navigated pointer that can register that it is touching the surface of an object, and use a camera (e.g., imaging device 106, which in some embodiments, may be configured with and/or connected to UE 102) to capture the location of a navigation of the surface and translate it to navigation (or navigational, used interchangeably) space. In some embodiments, such navigation space can correspond to, but is not limited to, sagittal, coronal and axial spaces; x,y,z space, 3D space, and the like, for example.

As discussed below, in some embodiments, the navigation space can be utilized to analyze a pre-operative image, and determine a pose estimation of the spinal anatomy of the patient being examined. According to some embodiments, the image can be a three-dimensional (3D) image (e.g., a CT, MRI, and the like), a two-dimensional (2D) image (e.g., intra-op fluoroscopy, for example), and/or a pre-op calibrated biplanar AP/Lateral (e.g., EOS Imaging, an image capturing a vertebral body surface of point clouds via a surface normal and/or intra-op surface touchpoints from the navigated pointer).

According to some embodiments, as discussed below, a user interface (UI) can be provided, which can be displayed on UE 102. In some embodiments, the UI can receive UI-prompted user annotations on pre-op and/or intra-op images, and algorithmically determine and output recommended intra-operative orientation parameters of the UE 102 (e.g., a C-Arm of the robot, such that the subsequent generated fluoroscopy images can be optimized to improve the likelihood of convergence of 2D/3D merge algorithms). According to some embodiments, as discussed herein, this can improve the initialization parameters for the execution of a 2D/3D merge algorithm, and thereby improve the signal-to-noise (S2N) ratio of individual vertebrae and their constituent components.

According to some embodiments, Process 300 begins with Step 302 where engine 200 identifies and analyzes a medical image of a patient. According to some embodiments, Step 302 can involve the capturing and processing of a medical image (e.g., a 2D/3D image, such as a MRI or CT, for example). In some embodiments, the medical image may be a previously captured medical image (e.g., pre-op), which is stored and retrieved.

It should be understood that while the discussion herein will focus on a single captured medical image, it should not be construed as limiting, as one of skill in the art would understand that the disclosed functionality of Process 300 (as well as the remainder of the instant disclosure) can be implemented for any type of image capture, which can include a set of medical images, video, live-streamed content, augmented reality (AR)/virtual reality (VR) content, and the like, without departing from the scope of the instant disclosure.

In some embodiments, Step 302 can involve engine 200 performing automatic segmentation (or auto-segmentation, used interchangeably) of the medical image. That is, according to some embodiments, engine 200 can computationally analyze the medical image, and segment the portions of the image that correspond to each bone/component of the spine and/or anatomical landmarks of the spine. For example, engine 200 can determine an image segment (or slice, region or object) of a CT image that corresponds to the specific regions of the spine (e.g., cervical spine, thoracic spine, lumbar spine, sacral spine, respectively).

According to some embodiments, engine 200 can execute a U-Net (or UNet, which is a convolutional neural network (CNN)) application or model trained with cross entropy loss to perform the segmentation. In some embodiments, the segmentation can be performed according to a particular criteria (which may be included in the request), which can correspond to, but not limited to, specific regions of the spine, regions and/or types of bones in the spine, and/or other properties (e.g., gray level, color, texture, brightness, contrast, and the like), and the like, or some combination thereof.

In some embodiments, engine 200 can implement and execute any type of known or to be known image segmentation algorithm, technique or mechanism, including, but not limited to, thresholding, edge-based, region-based (e.g., active contours, level-sets, graph cuts, and watershed algorithms, and the like) watershed, clustering-based, neural network-based (e.g., FCN or CNN, for example), transfer learning, heuristic edge detection, probability-based (e.g., Gaussian mixture models, clustering, k-nearest neighbor, Bayesian classifiers, and shallow artificial neural networks, and the like) and the like, or some combination thereof.

According to some embodiments, engine 200 can perform the auto-segmenting of the medical image to create a surface mesh and/or point cloud of the spinal anatomy. According to some embodiments, engine 200 can execute differing algorithms on the medical image, whereby an output can be analyzed to determine congruencies and/or dissimilarities between each image. For example, the medical image may be analyzed by, but not limited to, a region growing algorithm, an atlas-based algorithm, and a CNN, whereby an output can be provided via a merge algorithm, which determines congruencies as the output image, which enables the generation of the surface mesh and/or surface point cloud.

According to some embodiments, the auto-segmentation performed by engine 200 can enable the exposition of the anatomy of the patient, whereby engine 200 can utilize a Tactile Elastomer to create a vertebrae point cloud.

In some embodiments, engine 200 can utilize an iterative closest point algorithm to register an intra-op point cloud to a pre-op CT point cloud. According to some embodiments, the iterative closest point algorithm can be initialized based on based on software prompts of an anatomy of interest followed by user placement of a Tactile Elastomer tool on the anatomy of interest. For example, software prompts enable identification of, but not limited to, left facet or right facet, which can be enabled via user placement, software determination and placement, and like, or some combination thereof.

According to some embodiments, the auto-segmentation can involve a 2D/3D registration, which can be provided via engine 200 executing a reference 2D/3D merge algorithm for display within the provided UI, as discussed above.

Figure 4A:
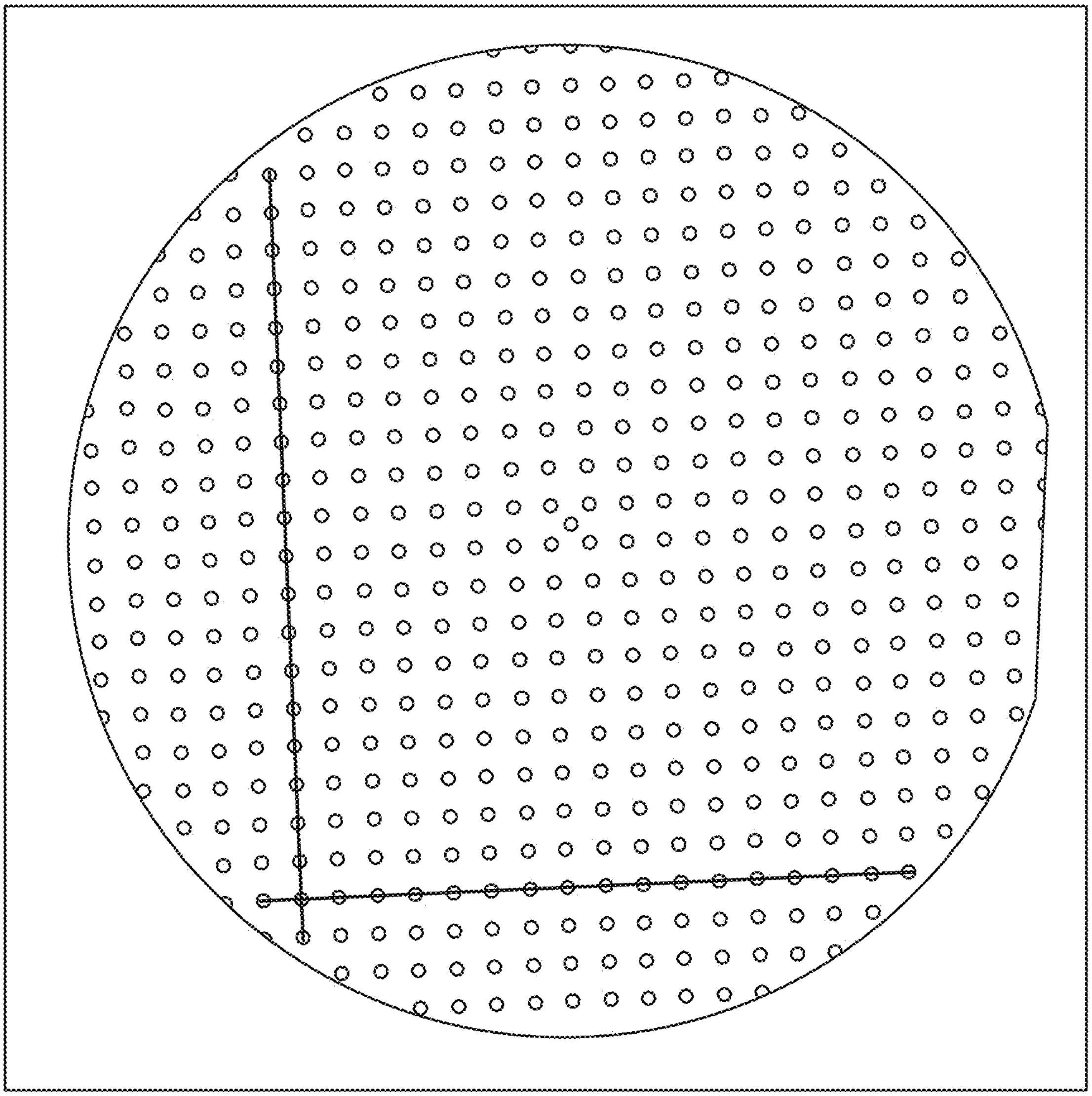

Thus, turning to FIG. 4A, provided is an example of an anterior-posterior (AP) or lateral fluoro-image. In some embodiments, with reference to FIGS. 4A and 9A, the C-Arm (or C-Arm fixture) of the depicted robot (in FIG. 9A) can utilize a trackable array via a grid pattern on a film, with radiopaque beads at a known distance from an intensifier associated with the C-Arm.

Thus, according to some embodiments, Step 302 can involve the initial registration of the patient tracking array to the anatomy of the patient. Accordingly, in some embodiments, the registration of the patient's spine can be performed.

In Step 304, engine 200 can determine an optimal location for surface-based registration. According to some embodiments, Step 304 can involve auto-segmentation of the medical image. In some embodiments, the segmentation of the image from Step 302 can be utilized.

In some embodiments, engine 200 can algorithmically identify an anatomical area of non-congruence (e.g., an area with a high number of discordant points that are ascertainable within the field of view of the Tactile Elastomer) within expected exposure site (e.g., pulled from auto-segmented medical image) that has greatest likelihood of convergence via execution of an iterative closest point algorithm.

In some embodiments, Step 304 can further involve the display, within UI, the area of interest to a user, whereby a prompt can be provided to place Tactile Elastomer on an identified site.

Turning to FIG. 4B, in some embodiments, depicted is a display on a UI that displays a previously generated AP or lateral fluoro image, which can receive user labeling of anatomical features of endplates and centroids of each vertebral body. Accordingly, the information under the "lateral shot" can include, the prompted information, and/or determined information from the provided medical image that was segmented.

In some embodiments, FIG. 4C provides a non-limiting example of the processing performed on the image from FIG. 4B. In some embodiments, engine 200 can receive the image from FIG. 4B, then output the FIG. 4C image, whereby engine 200 can receive user generated lines, and output an optimal lateral orientation (wag angle) of C-Arm in lateral C-arm position from the AP fluoro shot, whereby engine 200 can further determine an optimal orientation (e.g., Ferguson angle) of C-Arm in an AP position (from the lateral fluoro shot).

According to some embodiments, the UI can display a separate UI to be interacted with by an X-Ray technician, whereby an optimal orientation can be calculated in a similar manner as discussed above to generate the fluoroscopy shots. According to some embodiments, optimal AP and/or Lateral shots can be determined and/or taken for each vertebral body.

According to some embodiments, C-Arm images can be de-distorted to account for effects of magnetic field on the fluoroscopically generated image. For example, the images from FIG. 4A can be distorted de-distortion feature associated with the C-Arm.

According to some embodiments, engine 200 can execute and/or implement a dynamic re-registration and reconfiguration (DRR) search initialization, which can implement a rotationally centered spinous process and a parallel trajectory to the superior and inferior endplates for finding an appropriate AP fluoro shot.

According to some embodiments, the DRR initialization can be based on a parallel trajectory with the superior endplate of each vertebral body, both in AP and Lateral. The angle of rotation between AP and Lateral DRR can be determined by the difference in orientation between the tracking array attached to the C-Arm De-distortion fixture during the timepoints of each generated image.

Figure 4D:
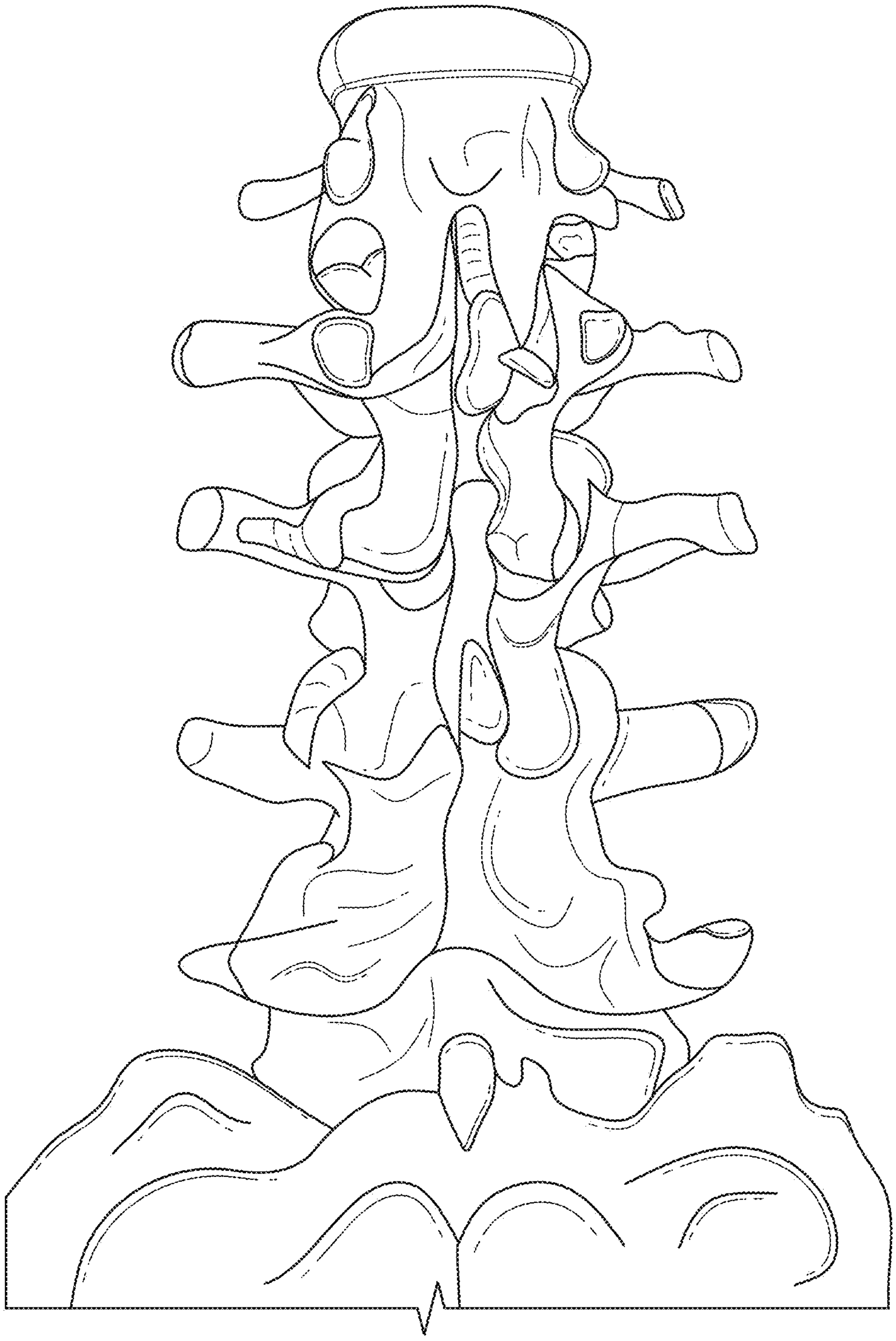
Figure 4E:
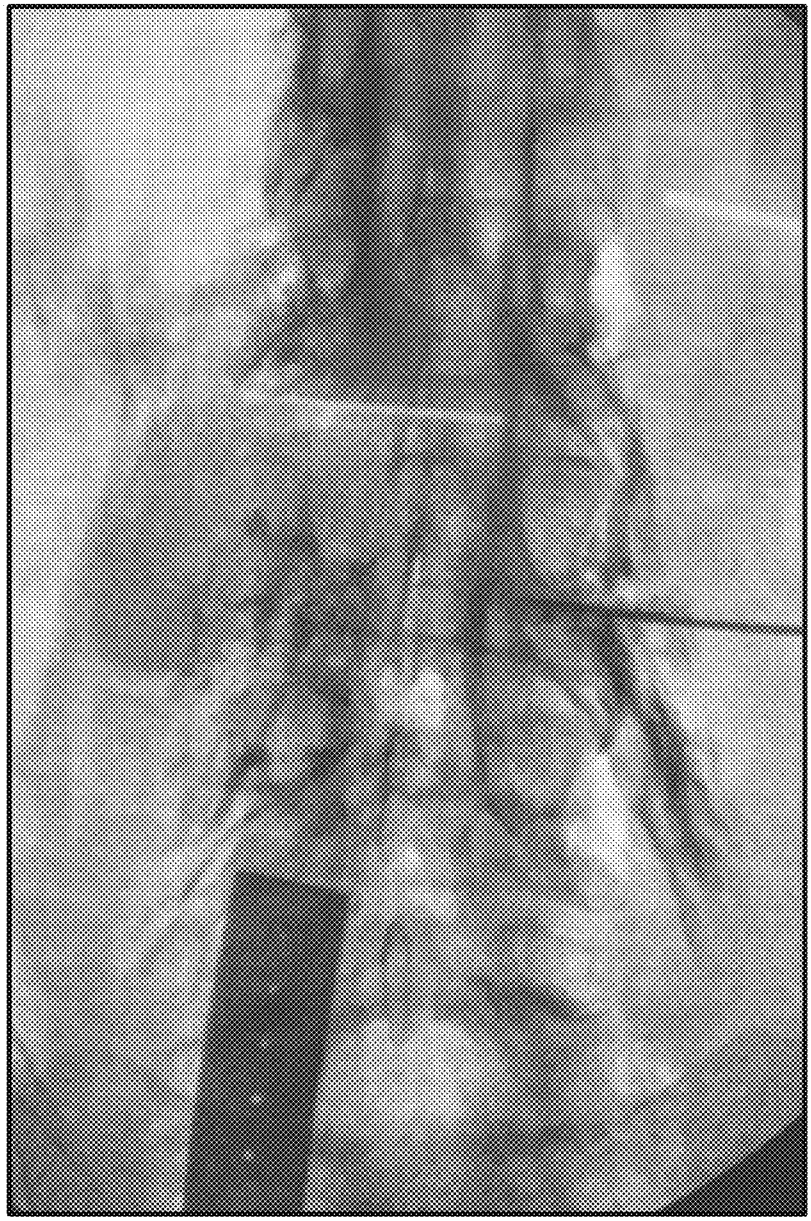

Turning to FIG. 4D, provided is an example of a rotationally centered CT image, whereby the alignment can be provided via DRR search, with matching fluoroscopy alignment, which reduces the convergence time and improves 2D/3D algorithm reliability. In FIG. 4E, depicted is an example of a rotationally aligned AP fluoroscopy with a spinous process centered between the pedicles.

According to some embodiments, engine 200 can generate iterative DRRs to determine/identify a DRR with an acceptable similarity score (e.g., comparison of pixel intensity matching between images to a threshold degree/amount), which can be translated/produced as an intra-op fluoro shot (or image).

According to some embodiments, once an acceptable DRR is identified, engine 200 can execute a 2D/3D merge algorithm to register the anatomical space in the medical image (e.g., CT scan, for example), to navigation space. In some embodiments, such analysis may be performed for each vertebral body level.

According to some embodiments, engine 200 can create an initial registration of the pose of a vertebrae utilizing keypoint detection of a fluoroscopy image mapped to an image (e.g., a CT, for example). With an initial registration and the simultaneous tracking of the patient via patient tracking array and C-Arm via C-arm cap tracking array, engine 200 can generate a live DRR simulation which outputs onto a UI the simulated DRR, which corresponds to the theoretical fluoroscopic image that would be produced based on the instantaneous pose of the C-arm relative to the patient at any point in time after the initial registration. According to some embodiments, the DRR simulator provides functionality for the surgeon or radiation technician to visualize live (e.g., in real-time) what an x-ray at that C-arm pose would look like in order to more quickly and accurately orient the C-arm to take additional x-rays, and thereby, among other benefits, reducing radiation exposure to the patient and OR staff and reducing time and expenditure of resources to acquire additional images.

In some embodiments, it may be desired to optimize the performance of the 2D/3D merge for the purpose of determining pedicle screw or interbody location within a 3D CT image post implantation. As such, in some embodiments, engine 200 can store the position of the navigated screw placement or navigated interbody placement, whereby the stored location of the aforementioned items can be used to initialize an auto-segmentation algorithm that segments all metal artifacts within the intra-op fluoro image. In some embodiments, lines can be provided (e.g., drawn by a user, for example) on the intra-op fluoro shot where the metal artifacts can be identified, and engine 200 can utilize such lines as initialization points to perform auto-segmentation of the metal artifacts. In some embodiments, the a computer-generated mask can be provided, which can be automatically and/or user adjusted. According to some embodiments, masking can eliminate areas of known discontinuity between synthetic DRR and intra-op fluoro shots for the purpose of improving the 2D/3D merge algorithm. Accordingly, in some embodiments, once a 2D/3D merge is complete, the UI can display a digitally reconstructed implant within a 3D image generated from pre-operative CT for analysis of safety of implant placement.

According to some embodiments, as discussed above, engine 200 can utilize a Tactile Elastomer. According to some embodiments, the Tactile Elastomer can be a innovatively configured Tactile Elastomer that can be a navigated instrument that can determine the surface topography of an object it is contacting (or in contact with).

According to some embodiments, the Tactile Elastomer instrument can be comprised of a distal elastomer that has the ability to deform, such that the instrument envelopes at least a portion of the surface it is touching. In some embodiments, the instrument can further include a reflective layer at the distal end of the elastomer that reflects the contours of the surface it is touching. In some embodiments, the instrument can further include an transparent rigid block that allows light to pass through and provides a backstop for the elastomer. According to some embodiments, the instrument can be enabled such that lights shine through the transparent block and onto the reflective layer.

In some embodiments, the instrument can further include a camera to capture the environment inside the elastomer to read the contours of the sensed surface. In some embodiments, the instrument can further include a printed circuit board (PCB) controller to control the camera and lights, and send the data captured to an external processor (e.g., another UE 102, for example).

In some embodiments, the external processor (e.g., additional UE 102) can process the surface topology data from the instrument to create a 3D surface, which can be compared to existing 3D model from another medical image (e.g., CT/MRI, for example). Accordingly, the processor, via execution of engine 200, can make a determination/merge the two datasets together, whereby a passive tracking array can be attached to the proximal end of the instrument such that it can be tracked in space by a camera.

Figure 4F:
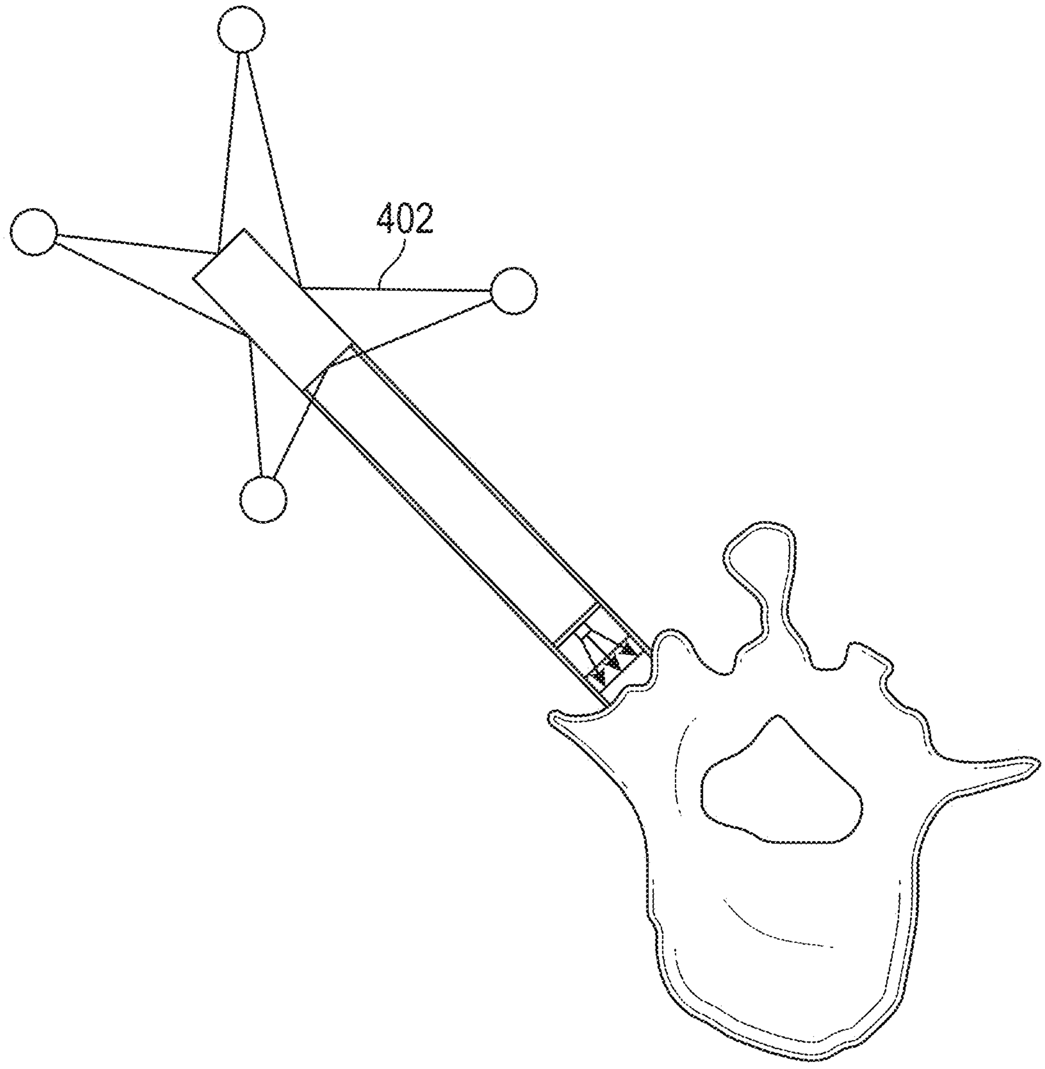

Turning to FIG. 4F, depicted is a Tactile Elastomer instrument reading the surface topology of a vertebral body. In this non-limiting example, the instrument can be inserted through a small incision in the skin with the elastomer at the distal end of the instrument. In some embodiments, the user drives the instrument through the incision to the vertebral body to touch off on bony anatomy.

Figure 4G:
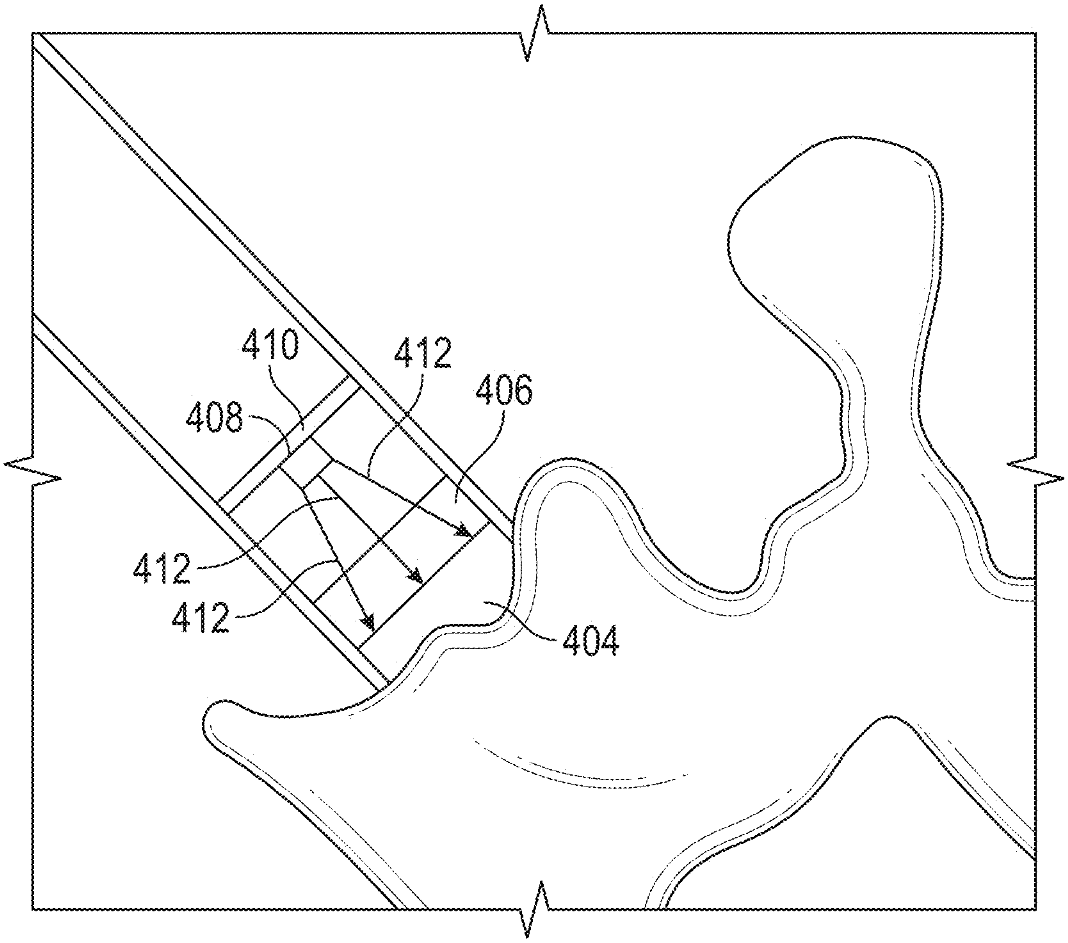

In FIG. 4G, which is a detailed view of the Tactile Elastomer touch sensing instrument in FIG. 4F, the tracking array 402 (shown in FIG. 4F) tracks the instrument pose within a navigation system. The elastomer 404 at the distal tip deforms to the anatomical surface it is touching (e.g., elastomer 404 is touching and deforming against the anatomy of the vertebral body, while the camera 408 is capturing the deformation with light 412 (e.g., via a provided and/or associated light source)). A reflective layer within the elastomer reflects the light 406 through the transparent backstop 406. The environment is captured by the camera 408 and the resulting data is transferred by the PCB board 410 to an external processor.

Figure 4H:
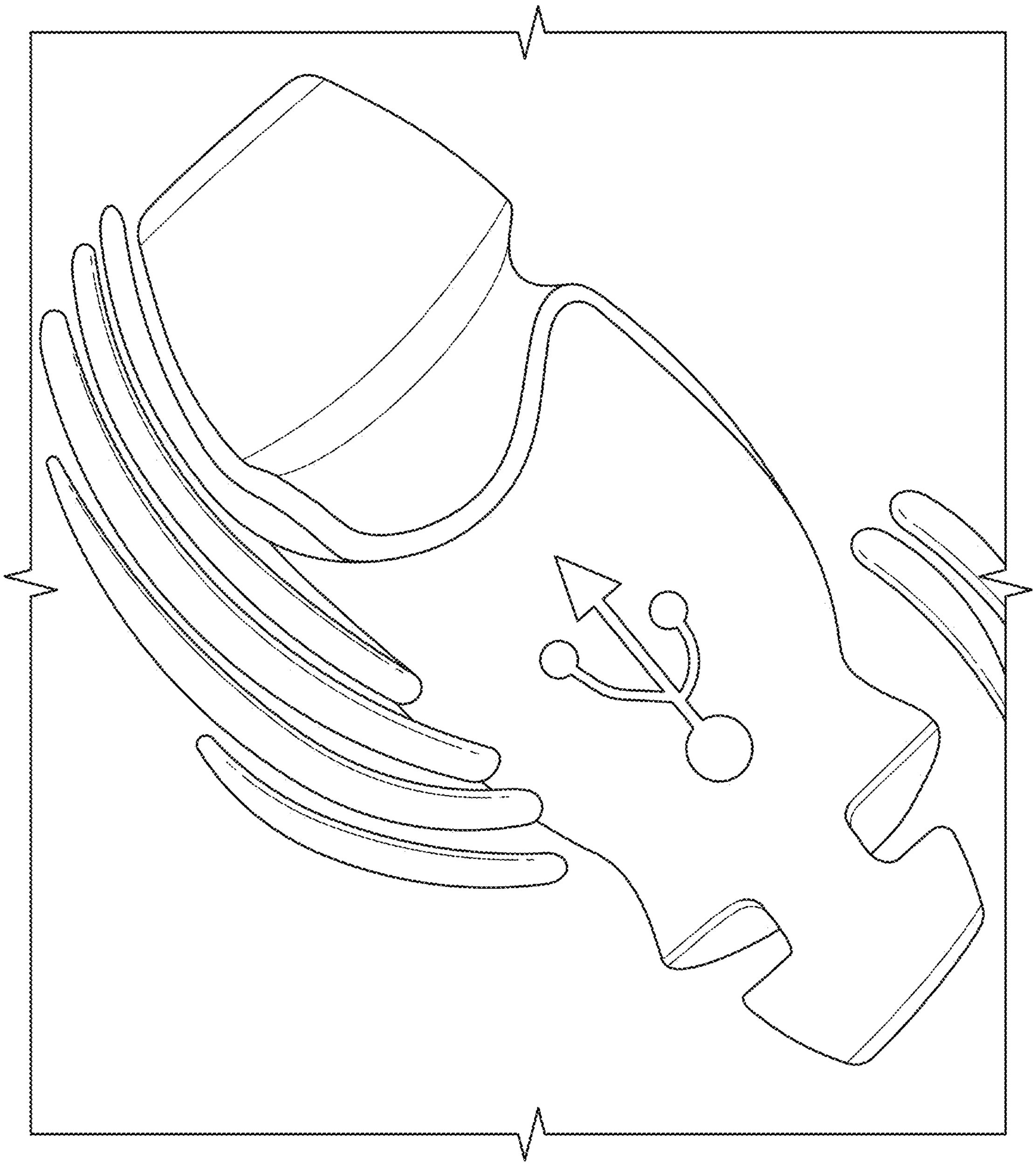

According to some embodiments, the instrument can be configured with and/or be associated with an external display/monitor that can display a live image captured by the instrument. Using the display, the user/surgeon can use the instrument until they identify surface anatomy that they believe will lead to a successful registration/merge at which point they can trigger the system to save an image to process into a point cloud and compare the pose estimation against an existing 3D model. An example of such captured image is depicted in FIG. 4H.

Accordingly, in Step 304, application of the Tactile Elastomer instrument can provide data for a site related to the spine, which can be analyzed via an iterative closest point algorithm, as discussed above. Accordingly, Step 304 can involve the registration of the spine based on the above analysis.

In Step 306, engine 200 can perform registration of the patient tracking array. In some embodiments, Step 306 can involve re-registration of the patient tracking array (e.g., from Step 302, as discussed above), which, for example, can correspond to a skin-marker, spinous process clamp, pedicle screw, posterior superior iliac spine (PSIS) pin, and the like.

According to some embodiments, Step 306 can involve engine 200 registering patient tracking array from a medical image via a 2D/3D merge or intraoperative CT (iCT), as performed in a similar manner as discussed above. In some embodiments, an open exposure of the spine may be required. In some embodiments, the performance of osteotomies, placement of pedicle screws and/or surgical maneuvers may be required.

In some embodiments, usage of the Tactile Elastomer to re-register vertebral body with pose initialization of an iterative closest point algorithm based on patient registration from patient tracking array can be performed. Such usage of the Tactile Elastomer can be performed in a similar manner as discussed above.

Accordingly, in some embodiments, a surgical maneuver can be performed (e.g., pedicle screw placement, osteotomy, and the like, for example). In some embodiments, the maneuver can be performed with or without a surgical robot (e.g., FIG. 9A robot, for example).

In Step 308, engine 200 can determine an accuracy of the surgical maneuver (e.g., pedicle screw placement). According to some embodiments, such accuracy determination can involve, but is not limited to, engine 200 registering a PSIS and/or spinous process tracking array of a medical image and/or 2D/3D merge. Accordingly, pedicle screws can be identified and/or placed.

In some embodiments, a tracking array can be attached to the pedicle screw, such that the tracking array is coincident with the screw shank and can ascertain pedicle screw position.

In a similar manner as discussed above, engine 200 can leverage the usage of the Tactile Elastomer to re-register a vertebral body with a pose initialization based on PSIS and/or spinous process tracking array pose estimation from prior registration. Thus, in some embodiments, engine 200 can determine placement of pedicle screw, and its accuracy therewith, based on updated vertebral body pose estimation and position of tracking array attached to pedicle screw.

In Step 310, engine 200 can create a vertebral body specific registration. According to some embodiments, Step 310 can involve creating a vertebral body specific registration with a pedicle screw and/or a spinous process tracking array, and a tracking alignment of spine in real-time via segmental tracking arrays.

According to some embodiments, Step 310 can involve, but is not limited to, auto-segmenting the spine from a medical image, as discussed above. In some embodiments, a previously auto-segmented model can be identified. Engine 200 can register a patient tracking array, as discussed above. In some embodiments, the performance of osteotomies, placement of pedicle screws and/or surgical maneuvers may be required.

In some embodiments, engine 200 can leverage the usage of the Tactile Elastomer to register a specific vertebral body to a tracking array attached to a vertebral body (e.g., pedicle screw or spinous process clamp, for example) with pose initialization determined via an iterative closest point algorithm based on initial patient tracking array. According to some embodiments, a specific vertebral body tracking can be of an auto-segmented vertebral body, and not entire spine.

Accordingly, in some embodiments, a navigated surgical maneuver can be performed (e.g., pedicle screw placement, for example), which can be executed with or without an autonomous robot, in a similar manner as discussed above. In some embodiments, multiple individual segments may be tracked to determine intra-operative alignment of spine in real-time.

In Step 312, screw and/or spine tracking, registration and navigation space information can be output via the UI, as discussed above.

Figure 5:
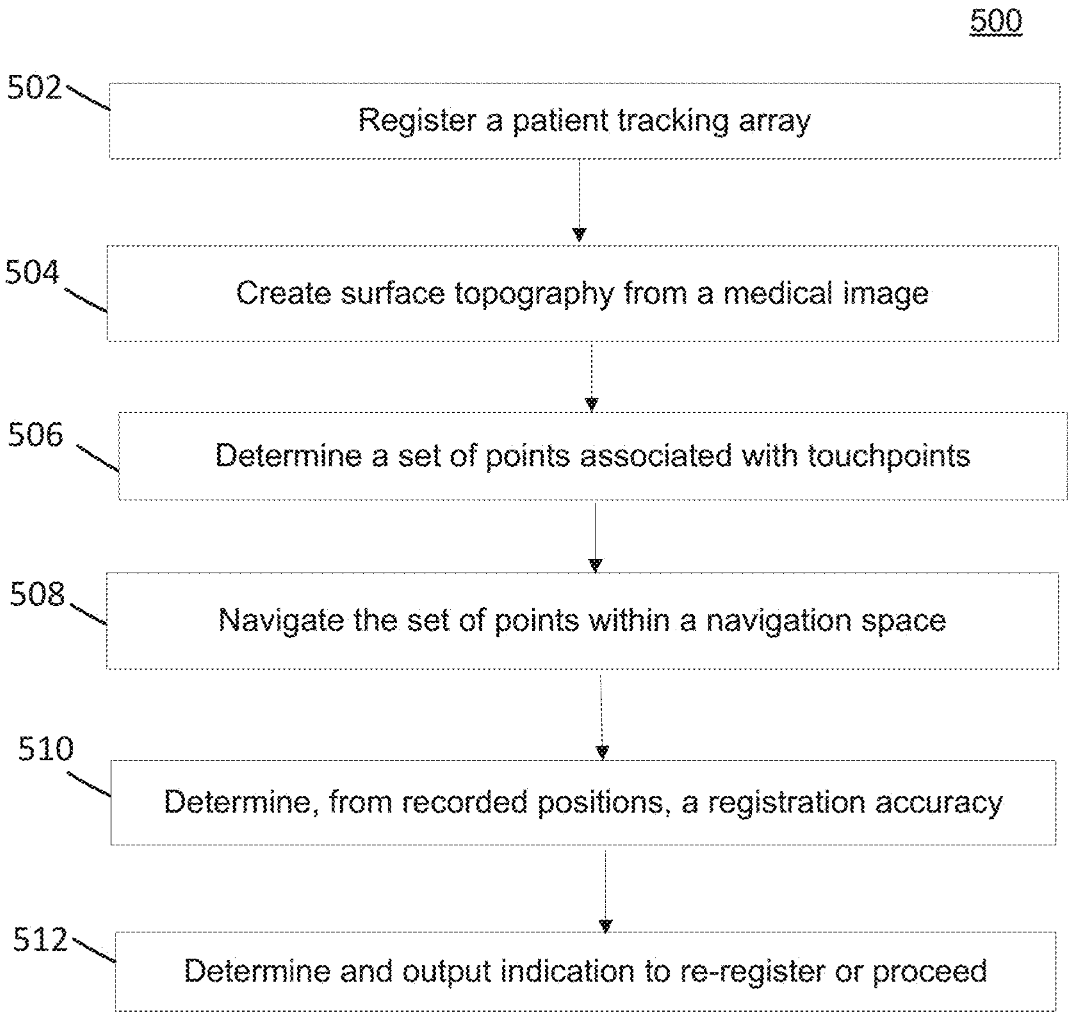
FIG. 5 illustrates an exemplary data flow according to some embodiments of the present disclosure.

Turning to FIG. 5, Process 500 is detailed which provides non-limiting example embodiments for determining the anatomical accuracy of an anatomical system from multiple touchpoints on a patient's bone anatomy.

According to some embodiments, Process 500 begins with Step 502 where engine 200 can register a tracking array. According to some embodiments, the registration can be performed via the similar steps discussed above at least in relation to Process 300 (e.g., via a 2D/3D merge and/or iCT, for example).

In Step 504, engine 200 can determine, create, generate, extract or otherwise a surface topography from a medical image. In some embodiments, the medical image can be associated with a pre-op image, and in some embodiments, the medical image can be a real-time captured image. For example, the medical image can be a pre-op CT scan of the patient.

According to some embodiments, an algorithm(s) may be executed in which a keypoint optimizer is trained in the form of a neural net to determine 3D keypoints that are visible at multiple vantage points of a c-arm projected fluoroscopy image. Autosegmentation of the vertebrae creates a point cloud or a surface model of spine. Additionally, surgical instrument(s) that are tracked by an external camera are inserted into the patient and are visible to intra-operative image like fluoroscopy when they touch the vertebrae. In some embodiments, this collision may be ascertained via a 6DOF force sensor on a robotic end effector, and in other embodiments the collision is determined via a haptic motor sensor. As a result of these actions the following data is available to a solver: instrument tip to vertebrae surface distance is negligible, initial pose estimate from a prior registration before instrument insertion, and segmented projected geometry of the metal tip. The following registration algorithm is then performed: first keypoints are ascertained for the vertebrae and instrument tip, then a solver that minimizes the loss of the instrument tip to vertebrae point cloud in combination with a solver that minimizes the loss of the keypoint detector of the instrument and vertebrae is performed to address the known z-axis inaccuracies of attempting single-shot keypoint registration. Finally, a similarity index is performed that finetunes this registration that does patch-based registration on the area of the fluoroscopy image that has the metal instrument and the vertebrae. The similarity index will compare a re-projected digital reconstructed radiograph with known tool position and the real fluoroscopy, and the resultant similarity measures will be converted to an estimated measurement accuracy of the relationship between the position of the instrument and the position of the vertebrae.

According to some embodiments, the known tool geometry of surgical instruments may be used in combination with a coordinate grid, with both being tracked in an external camera frame, to determine x-ray camera intrinsics when both geometries are visible in an x-ray frame.

A novel single-shot registration method is proposed where 10 or more 3D keypoints and their corresponding 2d projections via digitally reconstructed radiography to establish registration. 3D points are obtained from the preoperative or intraoperative 3D modality such as CT, MRI or bone MRI. These points can be selected at random or using an intelligent optimization method to select these points.

According to some embodiments, the anatomical keypoints identified in a keypoint optimizer may be used in combination with a coordinate grid or known tool geometry of surgical instruments to determine x-ray camera intrinsics when both geometries are visible in an x-ray frame. For this solver, both intrinsics and pose are solved concurrently. Additionally, multi-level segmental registration may be performed in which pose of a group of anatomic keypoints that belong to a non-deformable object such as a vertebrae are assumed to be fixed in relation to one another, and multiple registrations may be performed concurrently for multiple vertebrae whose pose is not assumed to be fixed relative to one another, but is assumed to be constrained to a particular range of movement as determined by kinematic population data. The groups of anatomical keypoints and their poses may be different from the preoperative CT, but the camera intrinsics solution for the set of solutions is assumed to be the same, thus resulting in both a set of solutions for the poses of the vertebrae as well as one solution for the x-ray camera intrinsics.

According to some embodiments, the surface topography can be created according to similar mechanics as discussed above—for example, engine 200 can utilize a Tactile Elastomer that is configured to be a navigated instrument that can determine the surface topography of an object it is contacting.

In Step 506, engine 200 can determine a set of points associated with touchpoints (e.g., from the Tactile Elastomer contact, for example).

According to some embodiments, Step 506 can involve algorithmically determining and identifying two or more points from the medical image, whereby the convergence point of planned pedicle screw with vertebrae can be separated, which can invalidate registration based on required registration accuracy acceptance criteria. In some embodiments, invalidation points may be ranked by absolute distance from convergence point.

In some embodiments, engine 200 can algorithmically determine and identify an anatomical touchpoint(s) from the medical image that will invalidate registration based on required registration accuracy acceptance criteria from single point of contact with Tactile Elastomers.

According to some embodiments, the algorithmic determination performed via Step 506 can involve engine 200 executing any type of known or to be known ML and/or AI algorithm or technology to perform such computational image analysis, such as, but not limited to, computer vision, neural network analysis, feature vector analysis, logistic regression, Hidden Markov Modelling, Bayes Theorem, and the like (in addition to any other algorithm discussed herein/above).

In Step 508, engine 200 can effectuate navigation of the set points within a navigation space.

According to some embodiments, navigated mechanical elements can be used to travel along lines required to touch pre-specified points, which can be recorded and record the position within the navigation space at which navigated mechanical element encounters mechanical resistance indicating an encounter with bone.

Figure 6:
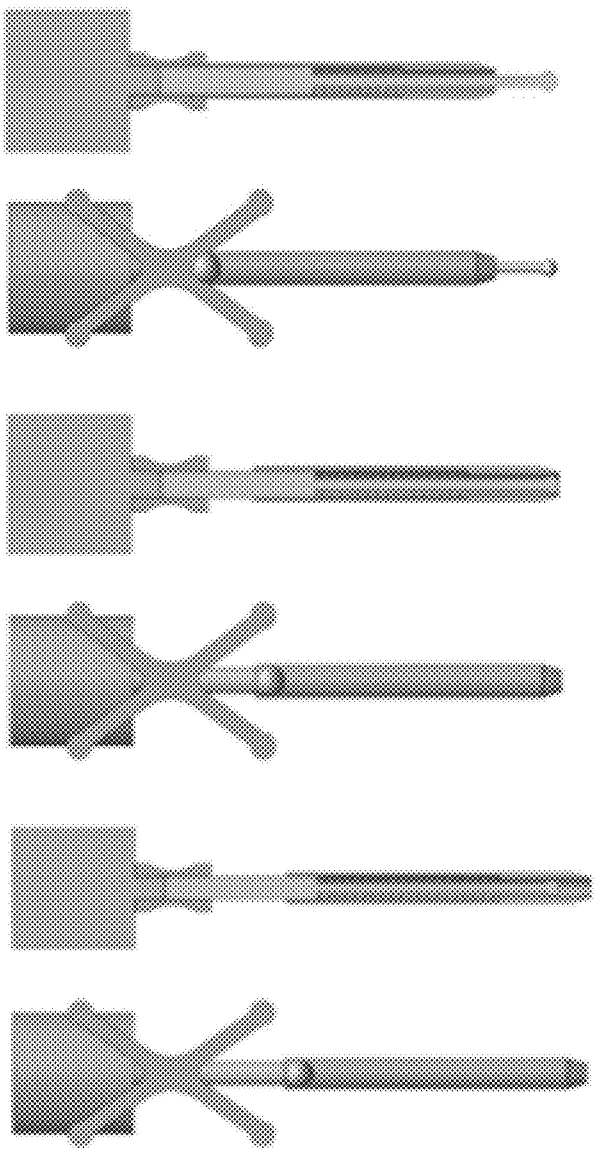
FIG. 6 depicts a non-limiting example embodiment for implementing the disclosed systems and methods according to some embodiments of the present disclosure.

In some embodiments, mechanical elements can include an end effector of concentric elements (e.g., multiple concentric dilators, or burr surrounded by concentric dilator, for example) that are independently tracked. In some embodiments, concentric elements can have different inner and outer diameters. In some embodiments, touchpoints can register as a circumferential area within the navigation space. An example of such embodiments is depicted in FIG. 6.

According to some embodiments, a mechanical element can be a burr connected to a navigated drill end effector. In some embodiments, determination that a collision has occurred can be via a six degrees of freedom (6DOF) force sensor attached to the end effector, or via torque, or some combination thereof.

According to some embodiments, a vibrating motor is attached at the fixed end of an anisotropic structure, such as a rod, which then vibrates in a circular motion. A monitor such as a3-axis accelerometer is also attached to the anisotropic structure. The resulting motion is then mapped electronically for analysis. With no force applied, a circular motion is achieved. When a net force is applied to the free, vibrating end of the rod, the circular pattern which is traced out becomes distorted, e.g., progressively flattened into an ellipse, in a repeatable way which is directly proportional to the applied force. The axis of the applied force can be ascertained according to the direction in which the ellipse forms. In this way, a determination can be made that a tool is touching bone or soft tissue based on the traced pattern change.

In some embodiments, a mechanical element can be a burr attached to a navigated drill that can be passed through a cylindrical drill guide end effector. In some embodiments, an indication can be leveraged that identifies the drill is on the surface of the vertebrae. In some embodiments, the indication can be computationally determined via engine 200, and in some embodiments, it can be provided by a user, or some combination thereof.

In some embodiments, a mechanical element can be a navigated pointer, whereby, in some embodiments, an indication can identify that the drill is on the surface of the vertebrae. In some embodiments, the indication can be computationally determined via engine 200, and in some embodiments, it can be provided by a user, or some combination thereof.

According to some embodiments, Step 508 can be performed via touch navigation by Tactile Elastomer on the surface, whereby the position can be stored within the navigation space along the point cloud generated by the Tactile Elastomer.

In Step 510, engine 200 can determine a registration accuracy. In some embodiments, engine 200 can computationally determine, from recorded positions of navigated element, whether registration accuracy meets acceptance criteria (e.g., an accuracy or distance threshold). In some embodiments, engine 200 can execute a ML/AI algorithm (as discussed herein) to determine if/when the point cloud matches expected surface topography point cloud generated from medical image (e.g., CT scan). For example, engine

200 can execute any type of known or to be known ML and/or AI algorithm or technology to perform such computational image analysis, such as, but not limited to, computer vision, neural network analysis, feature vector analysis, logistic regression, Hidden Markov Modelling, Bayes Theorem, and the like (in addition to any other algorithm discussed herein/above).

In Step 512, engine 200 can determine and provide an output (e.g., displayed on the UI, or audible output, for example) that indicates to the surgeon whether to proceed to re-register the patient (e.g., re-register the tracking array, for example). In some embodiments, the when the determined accuracy in Step 510 is at or above a threshold level (or outside an accuracy range), then the indication can alert the surgeon to re-register. If within the threshold (or range), then the surgeon can be alerted to proceed.

Figure 7:
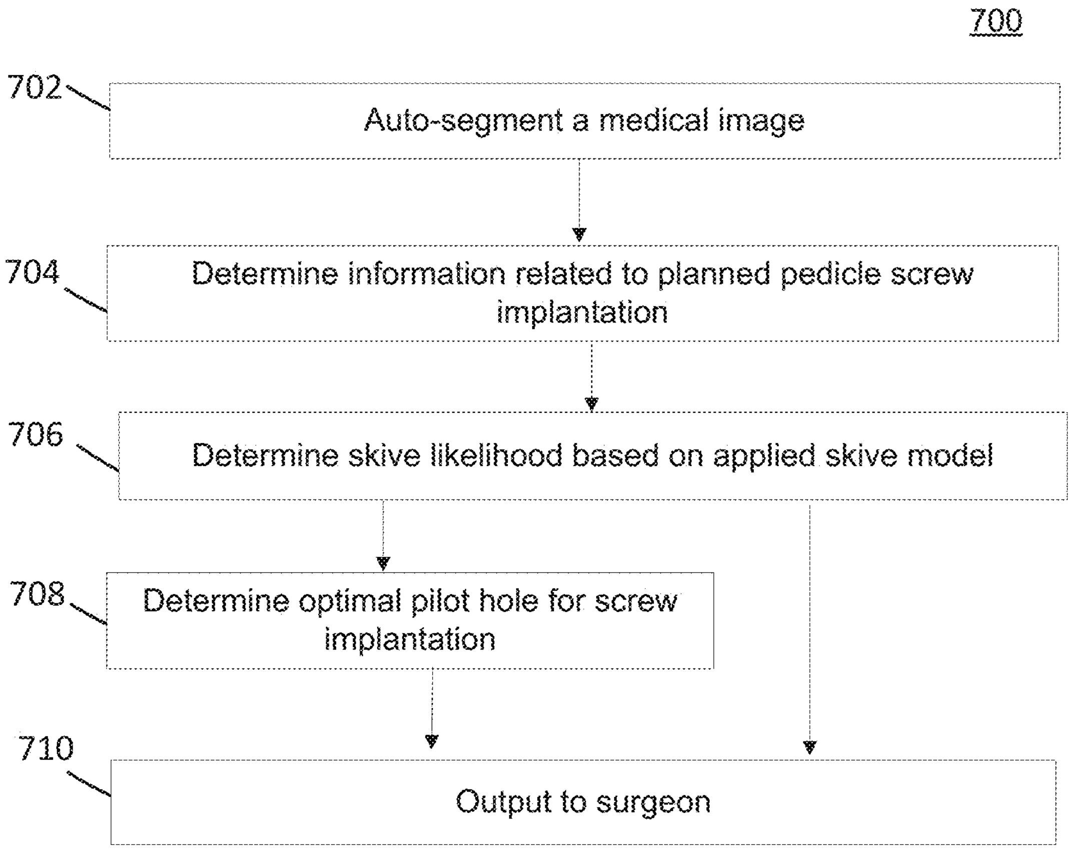
FIG. 7 illustrates an exemplary data flow according to some embodiments of the present disclosure.

Turning to FIG. 7, Process 700 provides non-limiting example embodiments for the automatic placement of pedicle screws via an autonomous robot (e.g., surgical robot). In some embodiments, Process 700 enables the placement of screws based on a determined instrument skive likelihood based on a planned pedicle screw trajectory. In some embodiments, Process 700 enables the determination of an optimal pilot hole size for implantation of the pedicle screw(s), which can be based on skive likelihood.

According to some embodiments, Process 700 begins with Step 702 where a medical image is auto-segmented by engine 200. This can be performed in a similar manner as discussed above. In some embodiments, a previously auto-segmented model can be retrieved; and in some embodiments, auto-segmentation can be performed on a captured medical image.

In Step 704, engine 200 can determine information related to a planned pedicle screw implantation. According to some embodiments, the determined information can include, but is not limited to, an angle of incidence of the planned pedicle screw trajectory on surface topography of the pedicle screw. In some embodiments, the surface topography information can be retrieved and/or determined in a similar manner as discussed above. This surface topography information can be compared to the implantation angle of the screw from the planned trajectory, and the determined angle of incidence can be determined. The analysis performed for Step 704 can be performed via any of the above mentioned ML/AI algorithms, among others.

In step 706, a skive model, which can correspond to a patient' spine and/or other information related to the spinal surgery, angle of incidence and/or planned trajectory can be identified, and utilized to determine a skive likelihood.

In Step 708, an optimal pilot hole for the screw implantation can be determined by engine 200. In some embodiments, engine 200 can analyze the skive likelihood in accordance with the angle of incidence, and determine an optimal hole for the implantation of the pedicle screw. In some embodiments, the optimal pilot hole can be based on additional or alternative inputs, which can include, but are not limited to, bone density, convexity of the surface, and the like, or some combinations thereof.

In Step 710, an output can be provided to the surgeon. In some embodiments, the output can be provided on a UI, whereby the output can be based on the information determined from Step 706 and/or Step 708. In some embodiments, therefore, the output can be a displayed interface that provides digital/virtual information related to screw-tip placement, which can be based on the skive model and/or pose invalidation algorithm (as discussed above).

Figure 8:
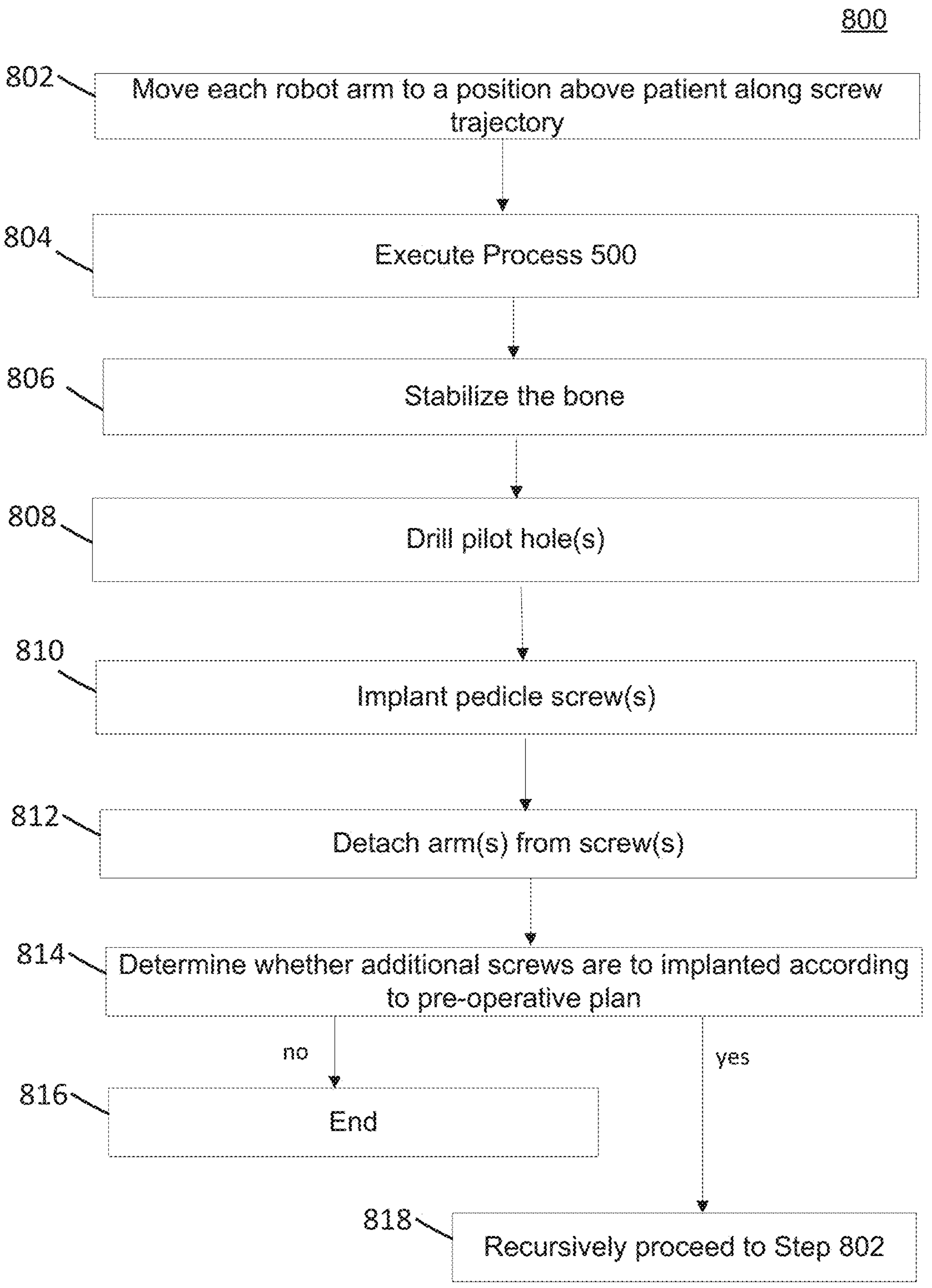
FIG. 8 illustrates an exemplary data flow according to some embodiments of the present disclosure.
Figure 9A:
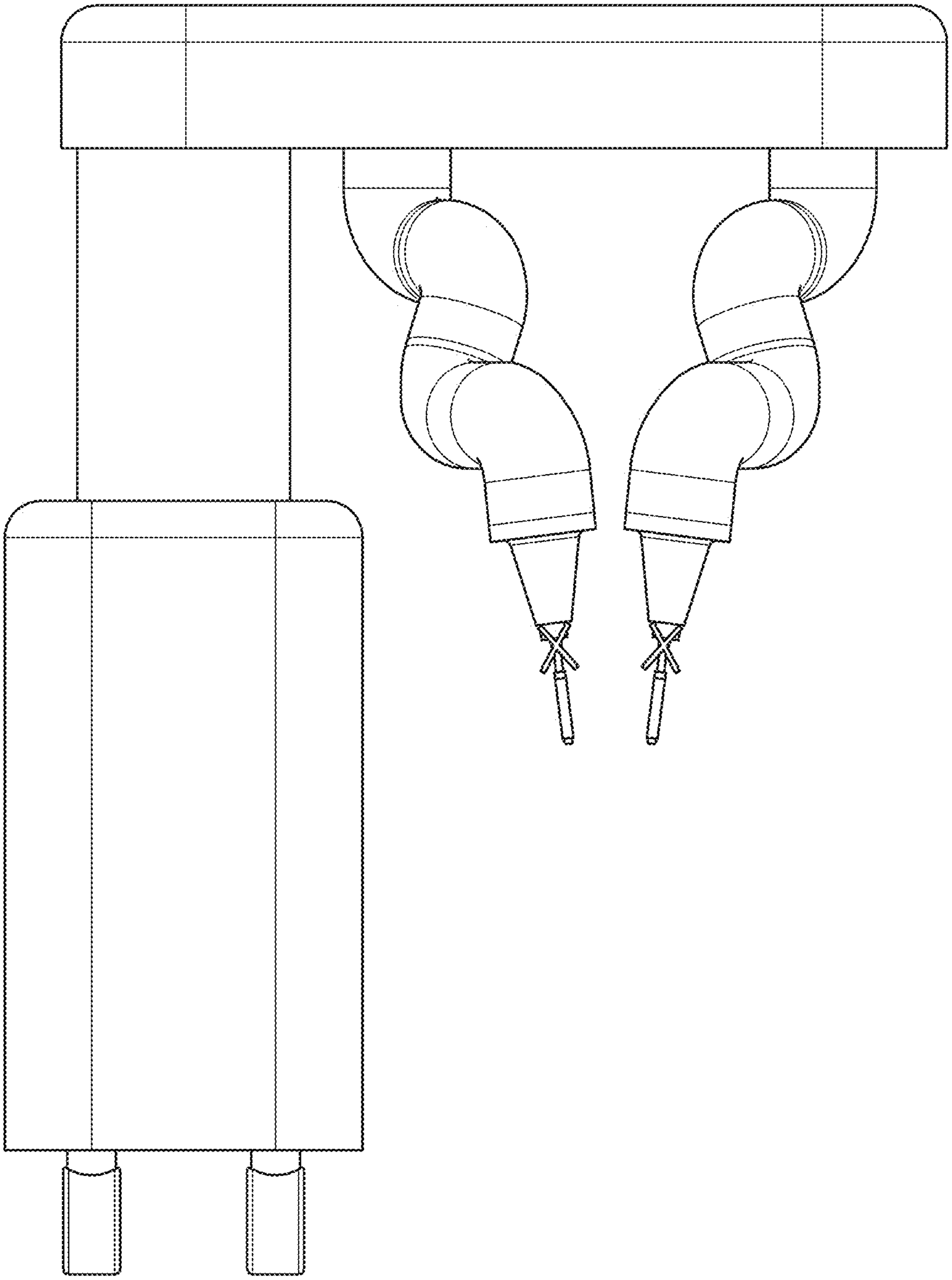
FIGS. 9A-9C depict non-limiting example embodiments for implementing the disclosed systems and methods according to some embodiments of the present disclosure.

In FIG. 8, Process 800 provides non-limiting example embodiments for a workflow and sequence for placing autonomous robotically placed screws with a two-armed robot (e.g., the robot depicted in FIG. 9A).

According to some embodiments, Process 800 begins with Step 802 where engine 200 each robot arm is moved to a position above a patient along a screw trajectory. The position and screw trajectory can be based on a preoperative plan and any of the information derived from the above mentioned processing.

According to some embodiments, a dovetail feature on the robotic end effector guides a skin knife to the surface of the vertebral body bilaterally. In some embodiments, end effector can point a laser to mark the location on the skin where the surgeon should create a skin incision. On each side, the surgeon creates skin incision, dissects and dilates down to the spine. The last dilator features a funnel style opening to guide the dilator into mating with the robotic end effector with a tracking array to be captured by the navigation system.

In Step 804, engine 200 can execute Process 500, as discussed above, to determine the anatomical system accuracy.

In Step 806, engine 200 can cause the robot to leave both drills at the surface of the bone to stabilize the segment.

In Step 808, upon stabilization, pilot holes can be drilled according to the number of planned screw implantations; and in Step 810, the robot can then implant the screws in the drilled pilot holes.

According to some embodiments, the robotic end-effector may drill the bone such that it creates a uniform hole concentric to the trajectory axis. In some embodiments, alternatively, the burr may be moved in a concentric sweeping motion to create a larger hole on the surface of the vertebrae of any size centered about the trajectory axis to prevent skiving of the screw, followed by plunging the burr straight through the bone such that it creates a hole concentric to the trajectory axis. In some embodiments, the pilot holes may be determined pre-operatively, as discussed above in relation to Process 700, and/or may be determined by a user.

In some embodiments, after a first pilot hole is created, the end effector drill remains in the bone as an anchor point while the second arm repeats the process for the contralateral side.

Once both pilot holes have been created, one at a time while the other arm remains anchored in the bone, each robot arm will switch end effector tool to a tap screwdriver to place the screw along the trajectory.

Accordingly, in some embodiments, the robot arm will advance the end-effector drill that is attached to a screw along the trajectory to the surface of the vertebral body. Once it reaches a predetermined point above the pilot hole the end effector will begin rotating the screw at a constant rate and advancing toward the hole.

According to some embodiments, the arm can sense that it has entered bone when it has sensed a reaction force (at or above a threshold level) at the screw tip with a force sensor, as experienced by the 6DOF force sensor coupled to the end-effector drill, or by the joint torques experienced by the joint torque sensors in each individual robotic joint. In some embodiments, the arm can then utilize a control feedback loop to advance along the axis of the planned screw trajectory at an advancement rate that maintains a constant pressure as determined by the reaction force on the end effector drill.

According to some embodiments, one arm may remain anchored to a screw as the superior or inferior contralateral pedicle is being drilled.

In some embodiments, the arm can stop advancing when the screw reaches its preplanned location, the reaction force exceeds a certain threshold, and/or the reaction force falls below a certain threshold. Once the screw reaches is in final position, the arm can maintain attachment to the screw, utilizing the newly placed screw as the new anchor point while the second arm repeats the same workflow on the contralateral side.

According to some embodiments, with reference to Step 812, once both screws have been placed the arms detach from the screws. In Step 814, engine 200 can determine if additional screws are to be implanted according to the preoperative plan. If so, processing proceeds to Step 818, where engine 200 recursively reverts back to Step 802 to repeat the processing for the additional screws. If no, then processing ends at Step 816.

According to some embodiments, Process 800, via engine 200 controlling a surgical robot provided in FIG. 9A, can effectuate determinations of spinal flexibility. According to some embodiments, this data can provide a surgeon with intraoperative feedback to drive decision making on correction, techniques/maneuvers, magnitude of correction required, and effectiveness of correction maneuvers already performed, among other benefits.

According to some embodiments, engine 200 can pre-operatively, determine a range of motion by obtaining a pre-op medical image (e.g., CT, MRI and/or standing EOS film, for example) to determine vertebral body range of motion in different postural alignments (e.g., standing and supine). In some embodiments, range of motion may be further determined intra-operatively, by determining postural changes between the pre-op CT and intra-op positioning (e.g., prone or lateral decubitus).

According to some embodiments, when anchoring to the spine, either through burr insertion or through pedicle screw placement as previously described, the robot may manipulate the spine. In some embodiments, moving the end effector of the arm to a new position while still anchored to the spine can create a reaction force by the spine on each robotic arm that can be sensed via the joints of the arm or a force sensor in the end effector.

According to some embodiments, the robot may manipulate the spine through a predetermined range of motion to calculate a translation/rotation-force curve. This range-of-motion may be determined by the pre-operative or intra-operative scans in different postural patient alignments (e.g., prone, supine, standing, lateral decubitus).

In some embodiments, the surgeon may use this translation/rotation-force curve or curve comparison to a previously generated curve to determine the effectiveness of their surgical manipulations (e.g., osteotomy, soft-tissue release, discectomy) throughout the procedure. The translation/rotation-force curve may be used to determine an optimal rod curvature for the ascertainment of an optimal post-operative spinal alignment.

In some embodiments, important/useful surgical decisions that may be augmented by this intra-operative information can be, but are not limited to, intra-operative rod bend, determination of sufficiency of soft-/hard-tissue release, comparison of spine stiffness pre- and post-intervention, attainable segmental and global alignment, likelihood of adjacent segment disease via calculation of expected surgical forces the spine will encounter during rod reduction maneuver, and the like.

According to some embodiments, Process 800, via engine 200 controlling a surgical robot provided in FIG. 9A, can effectuate a determination of initial fixation strength. This data provides the surgeon with intraoperative feedback to drive decision making on correction, techniques/maneuvers, magnitude of correction required, and effectiveness of correction maneuvers already performed, among other benefits.

According to some embodiments, a surgical robot uses a vibrating motor that is attached at the fixed end of an anisotropic structure, such as a rod, screwdriver, tap, knife, burr, or drill which then vibrates in a circular motion. The vibration may be applied via the typical motor movements or a burr or drill. A monitor such as a 3-axis accelerometer is also attached to the anisotropic structure. The resulting motion is then mapped electronically for analysis. With no force applied, a circular motion is achieved. When a net force is applied to the free, vibrating end of the rod, the circular pattern which is traced out becomes distorted, e.g., progressively flattened into an ellipse, in a repeatable way which is directly proportional to the applied force. The axis of the applied force can be ascertained according to the direction in which the ellipse forms.

Figure 9B:
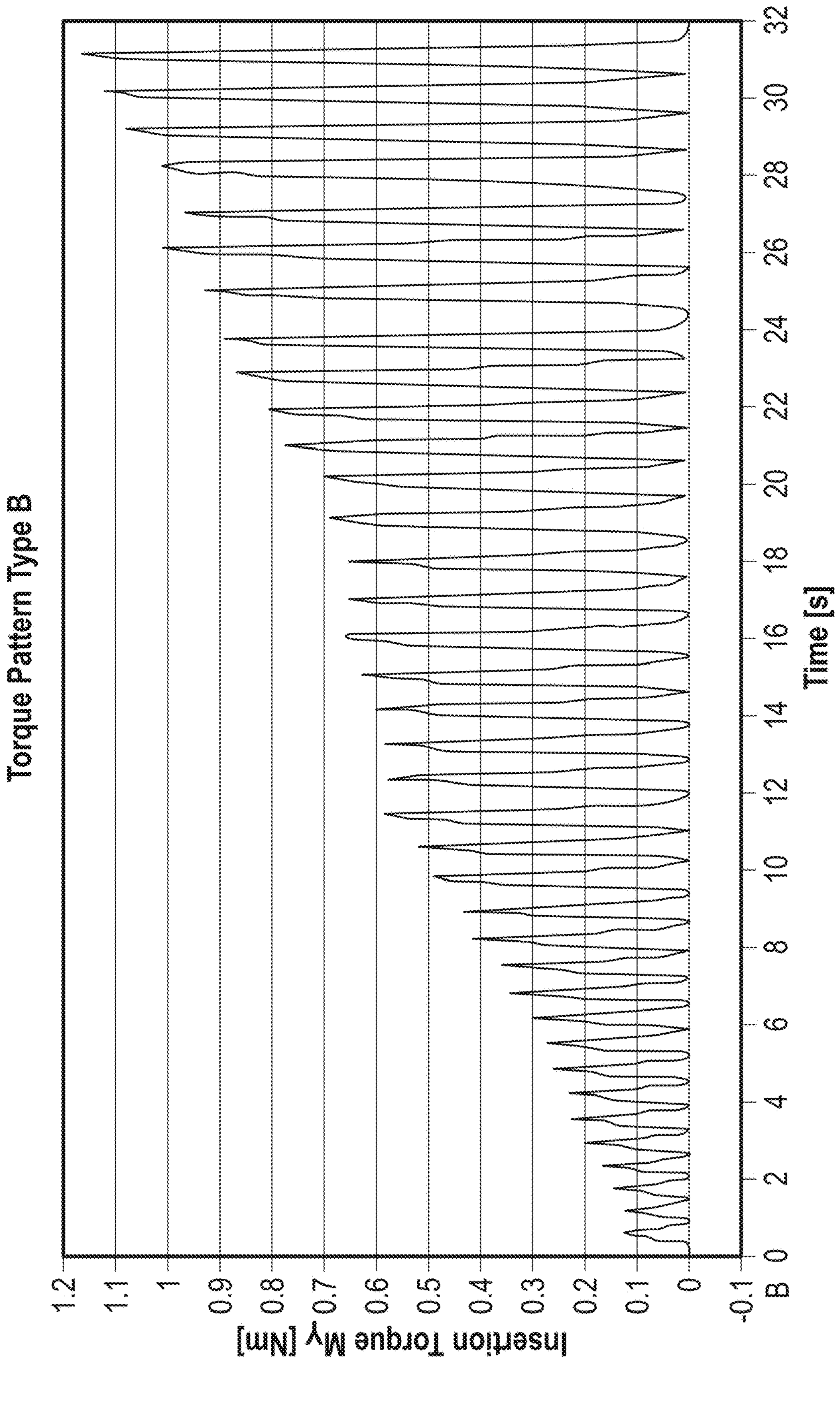

According to some embodiments, after a burr pilot hole has been created, an undersized tap relative to the planned pedicle screw (e.g., tap=4.5 mm, pedicle screw=5.5 mm, for example), or a pedicle screw, can be robotically drilled into the spine bilaterally. In some embodiments, the robotic end effector can store a torque-time graph when implanting the pedicle screw. An example of such is depicted in FIG. 9B.

In some embodiments, the robotic end effectors and/or vibration motor can then apply force to the implanted tap or screw such that the vertebrae is static but the tool may have micromotion $<1$ mm movement within the vertebrae. According to some embodiments, a force can be applied, whereby a displacement curve can be generated and stored from this applied force with the resultant movement of the tool within the static vertebrae.

In some embodiments, the force-displacement curve may be combined the insertion torque-time curve, as well as pre-operative patient characteristics that may include, but is not limited to, bone density, age, gender, frailty, hormonal status, and other relevant medical characteristics, to determine the likely pull-out strength and cyclic loading strength of the pedicle screw.

Additionally, in some embodiments, quantifiable geometric characteristics of the pedicle screw geometry, patient vertebral geometry generated from previous auto-segmentation, pedicle screw trajectory, screw material type (e.g., stainless steel, titanium, carbon fiber, and the like) may be included in the model.

In some embodiments, the expected forces from planned or intra-operatively perceived correction maneuvers can be compared with the modeled bone-implant structural integrity, and a warning may be generated to the user that the expected force of the correction maneuver exceeds the structural integrity of the implant interface.

Figure 9C:
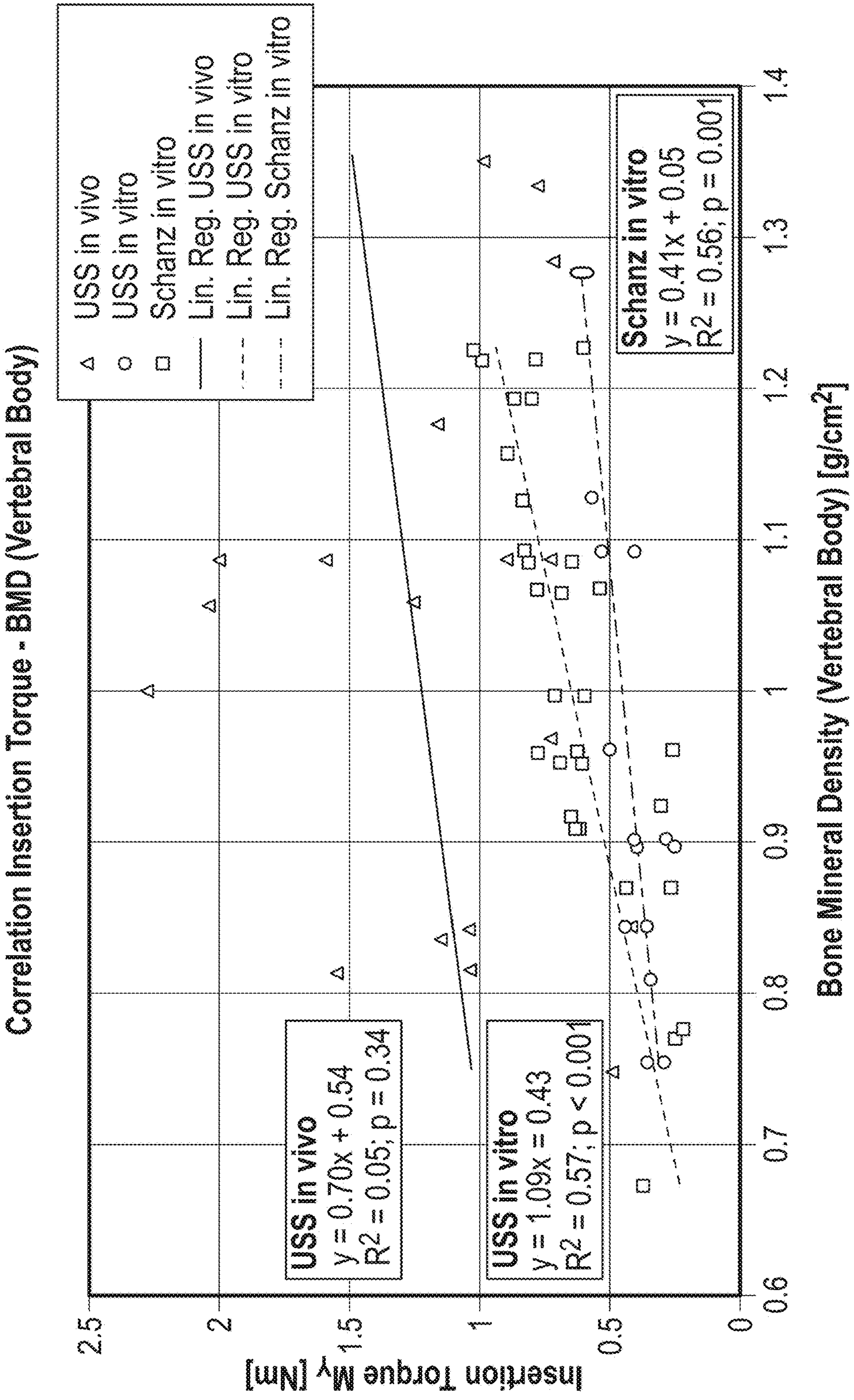

In some embodiments, this model will outperform simple insertion torque models, as these models have unacceptably high variance. An example of such is depicted in FIG. 9C.

According to some embodiments, Process 800, via engine 200 controlling a surgical robot provided in FIG. 9A, can effectuate sagittal, coronal, de-rotation and/or a combination of correction maneuvers to hold correction.

According to some embodiments, after placing all the pedicle screws, the robot can have the ability to reattach to a screw in the preoperative plan by returning to the trajectory within the reference coordinate system. When anchoring to the spine, either through burr insertion or through pedicle screw placement as previously described, the surgeon has the ability to use the robot to manipulate and correct the spine by unlocking and moving each arm. In some embodiments, this can be performed by autonomously correcting the spine using correction maneuvers created in the preoperative plan.

In some embodiments, based on the preoperative plan, the robotic arms, while anchored to different levels of the spine, can move into new desired positions for better alignment.

In some embodiments, force sensors in the end effector and/or joint torque sensors in the arm joints can sense the reaction force of the spine, and can end the maneuver when force sensed exceeds or falls below a predetermined threshold. In some embodiments, correction maneuvers can occur in any plane (e.g., coronal, sagittal, axial) or a combination of planes. In some embodiments, the robot can maintain correction while the surgeon places a rod on the contralateral side and locks the screws to the rod.

According to some embodiments, Process 800, via engine 200 controlling a surgical robot provided in FIG. 9A, can effectuate aid in interbody placement, which can increase reliability of interbody placement and reduce likelihood of violating endplates.

According to some embodiments, after placing screws at adjacent levels, the robot can reattach to screws such that one robotic arm is anchored to each of the levels. In some embodiments, the robot can then manipulate the bodies autonomously and/or be unlocked and manipulated by the surgeon and relocked to hold a position. In some embodiments, the correction can be tracked by the intraoperative planning software to give real-time visualization of vertebral body pose by tracking the end effector pose/robotic arm via the camera vision navigation system.

In some embodiments, force sensors in the end effector and/or the joints of the robotic arm can sense the reaction force of the spine and have the ability to unlock if/when the force sensed falls below or exceeds a certain threshold. In some embodiments, once the robot has positioned the vertebral bodies in the desired location, using navigated instruments, the surgeon can perform the discectomy and place the interbody device. In some embodiments, the force against the end plates during insertion can be measured by sensors on the end effector or in the robotic arm to determine likelihood of end plate violation.

Figure 10:
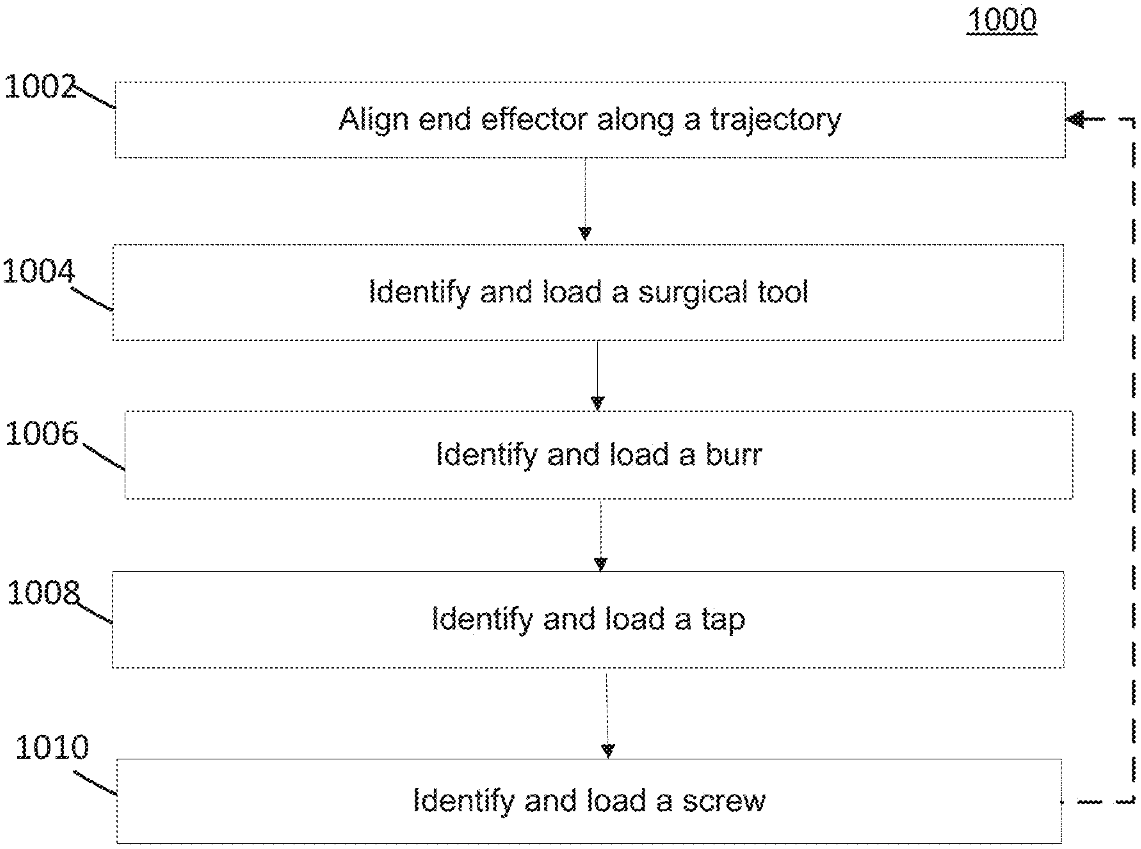
FIG. 10 illustrates an exemplary data flow according to some embodiments of the present disclosure.
Figure 11A:
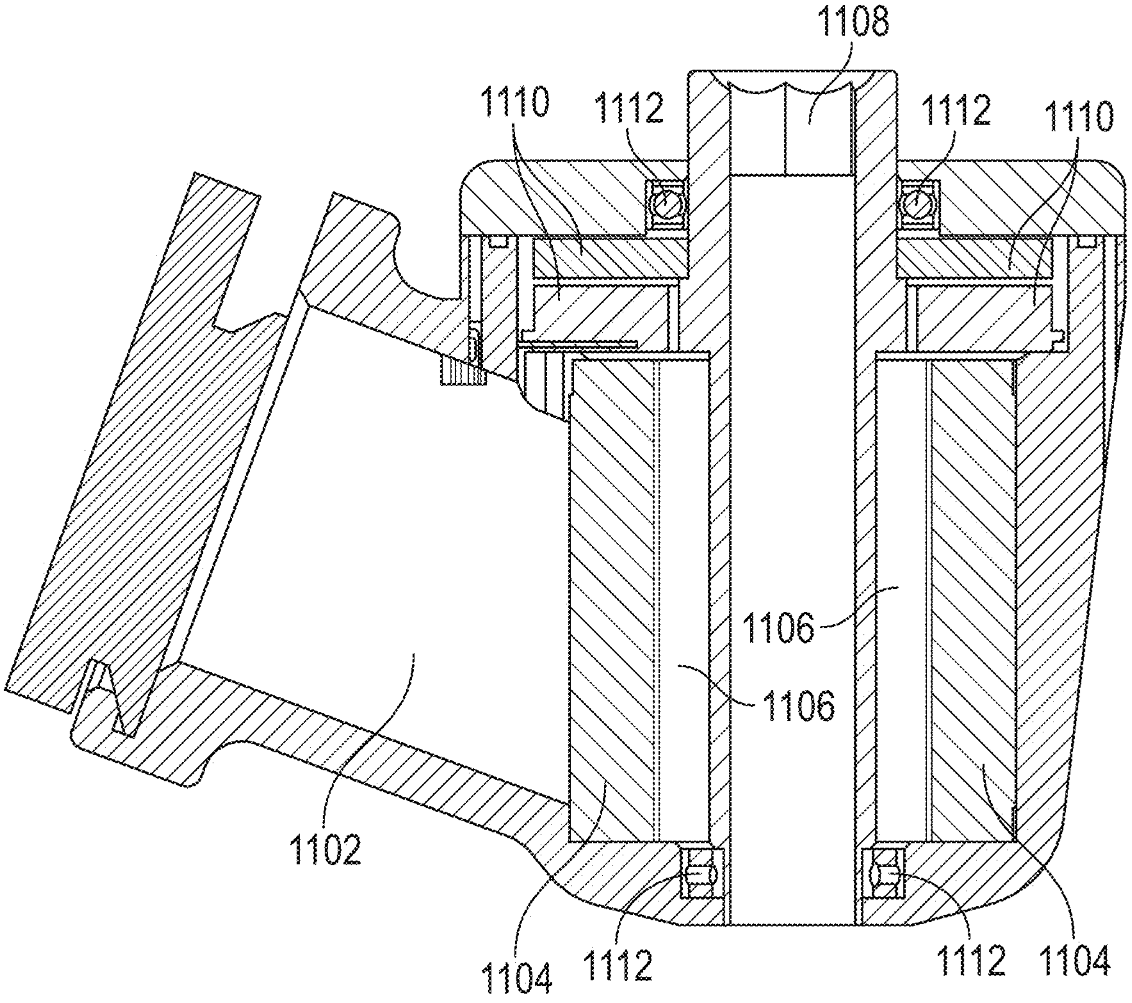
FIGS. 11A-11E depict non-limiting example embodiments for implementing the disclosed systems and methods according to some embodiments of the present disclosure.
Figure 11B:
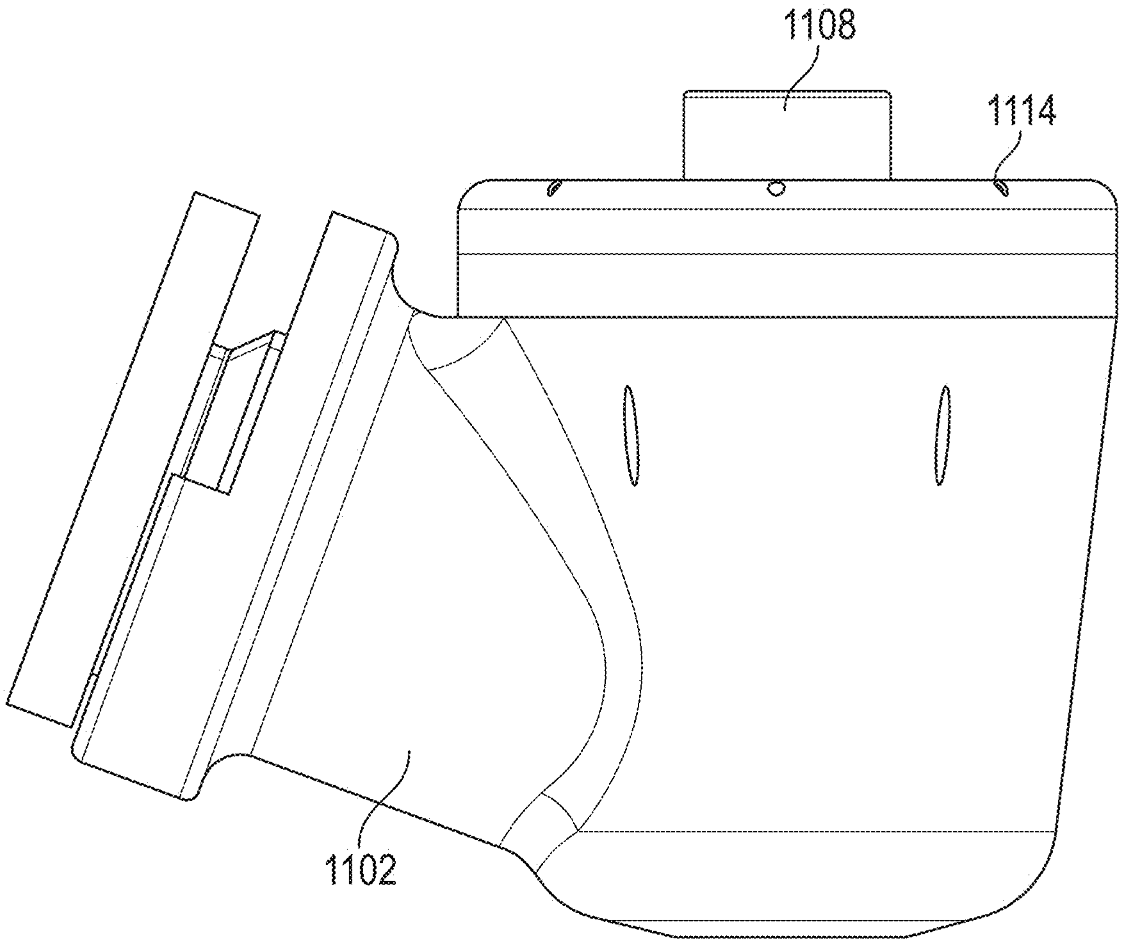
Figure 11C:
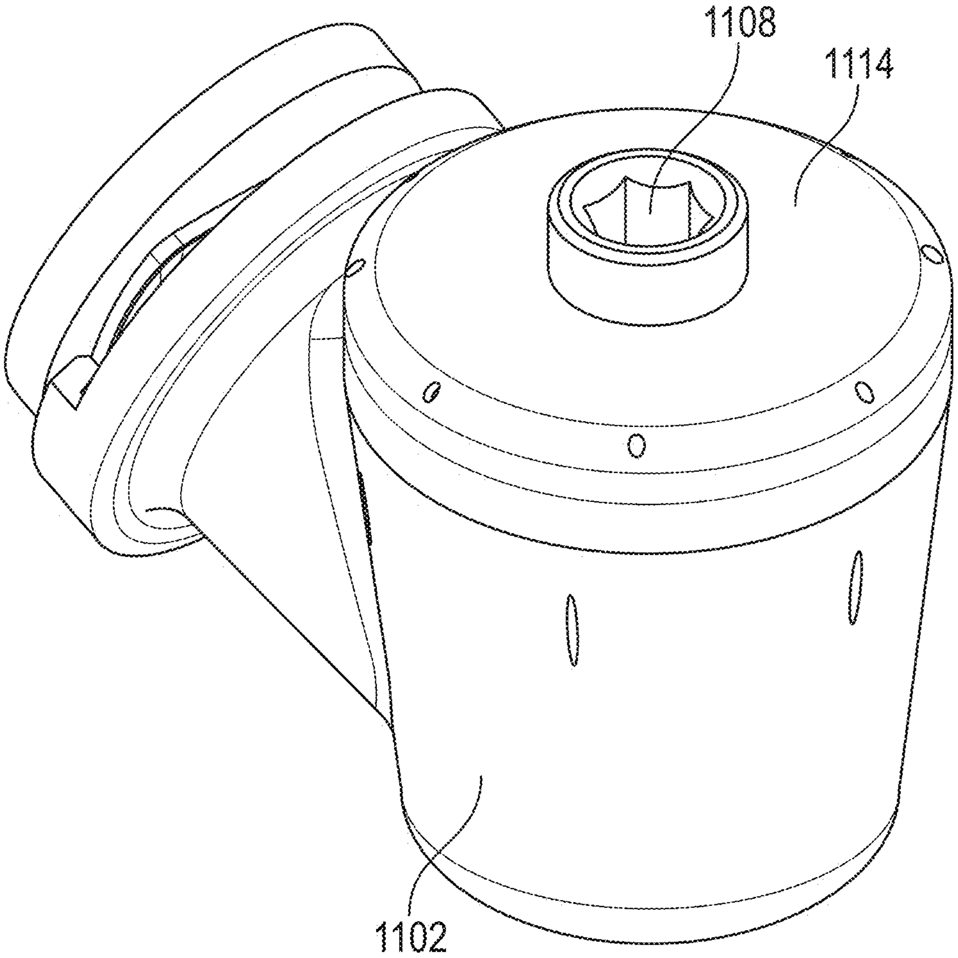
Figure 11D:
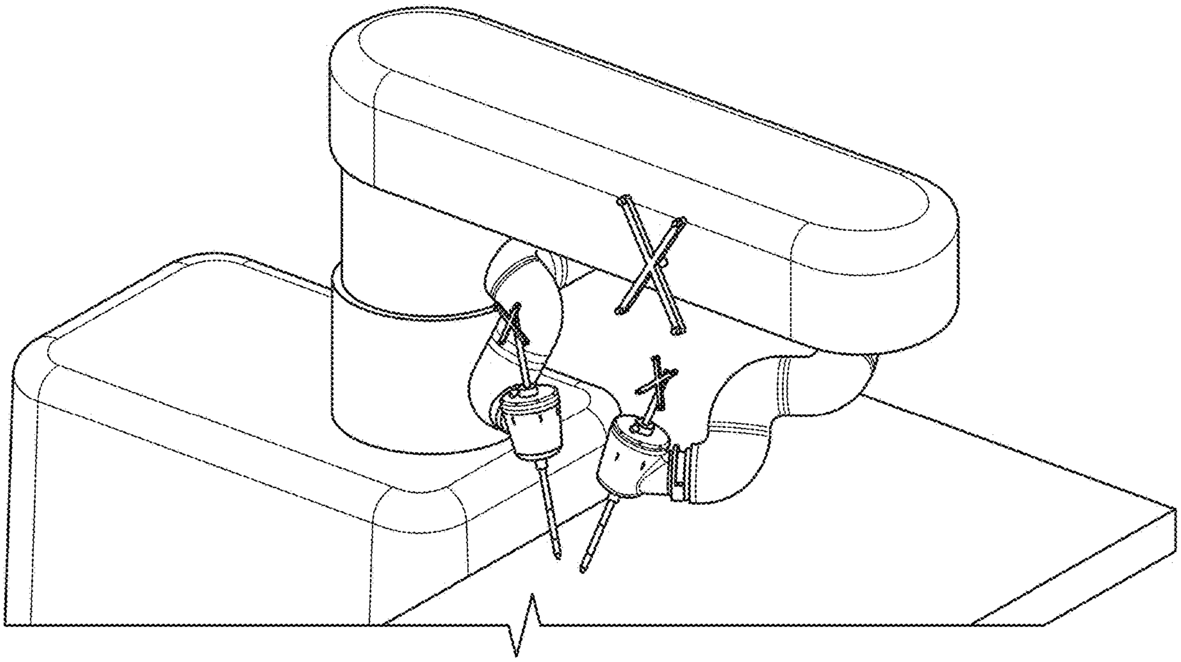
Figure 11E:
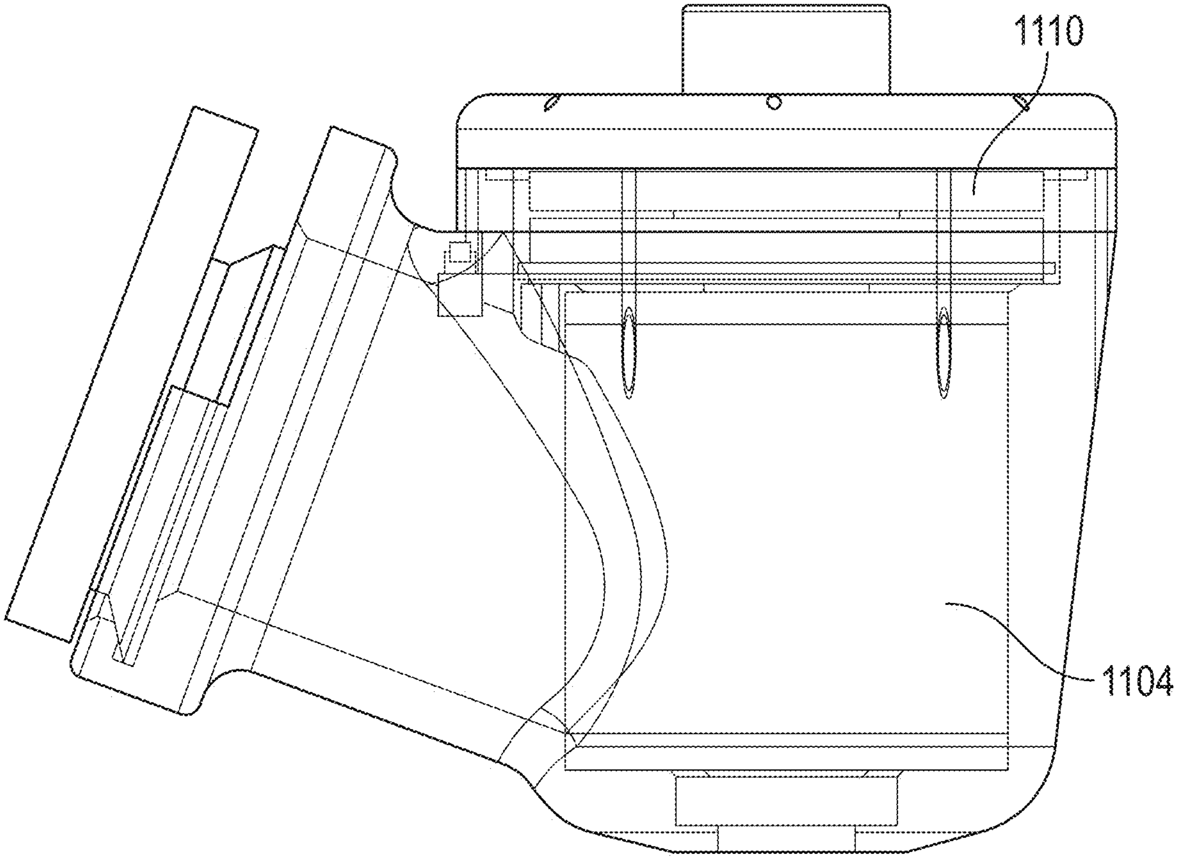

Turning to FIG. 10, Process 1000 is provided with details non-limiting example embodiments for placement of pedicle screws with a linear actuator end effector.

Accordingly, with reference to FIGS. 11A-11E, illustrated are different perspectives of an end effector. As discussed above, the end effector can attach to and manipulate tools for autonomous surgery.

According to some embodiments, the end effector can include a mounting interface to attach the end effector to a robotic arm, such that it rigidly connects the robotic arm to the tools. The end effector can also include a central lumen, including two main parts a rotor and a stator. The rotor can be rigidly attached to the mounting interface, and thus the robotic arm. The rotor can be concentric to the stator and can be in electromagnetic communication with the stator, such that varying electric currents to the stator will rotate rotor and thereby the engage tool.

According to some embodiments, a variety of known or to be known surgical tools (e.g., scalpel, drill, and the like, for example), can be inserted into the distal portion of the central lumen (or otherwise coupled thereto), which rigidly engages to the rotor such that its rotation can be driven by the rotation of the rotor. In some embodiments, the tool can be advanced toward the surgical site autonomously by the robotic arm, which simultaneously controls the rotation speed, direction, and position of the tool engaged to the end effector.

In some embodiments, the disclosed end effector can include a third component, such that the interface between the stator and the mounting interface is not a rigid body, but instead a linear actuator designed to translate the rotor, stator and tool along a linear trajectory. Thus, the robotic arm can stay stationary in space while the end effector, inclusive of a linear actuator, translates the rotational drive mechanism, which includes the stator, rotor and tool, while simultaneously controlling the linear and rotational speed, direction and position of the tool engaged to the end effector.

As depicted in FIGS. 11A-11E, in some embodiments, the housing 1102 connects the robot arm to the surgical tool. Inside the housing there is a rotary actuator comprising of a stator 1104 and a rotor 1106. The stator can be fixed to the housing and can include wire coils. The rotor can be a magnet in electromagnetic communication with stator such that a current supplied from the robotic arm to the stator causes the rotor to rotate. The rotor can be fixed to the central tube 1108. The relative speed and position of the rotor to the stator can be measured by an inductive encoder 1110. The central tube is held within the housing by bearings 1112, which stabilize and allow smooth rotation relative to housing. Central tube 1108 features goes through the entire housing such that a tool can be passed from the proximal to distal end. It features a female hex to rotate the tool with central tube and controlled by the robotic controller. The central tube locks the tool in place relative to the rotor. The cover 1114 seals the internals so that they are water and dustproof.

Turning back to FIG. 10, according to some embodiments, Process 1000 can involve an end effector of a robotic arm for spine surgery. In some embodiments, as discussed above, the end effector has an inner lumen that can interface with various surgical tools. The end effector has the ability to engage, disengage, advance, and retract the tools along a trajectory. The end effector is designed such that a tool such as a burr, awl, tap, or screw can be inserted through the proximal end of the lumen and linearly advanced along the axis of the lumen through the distal end, and toward the spine.

According to some embodiments, Process 1000 can begin with Step 1002 where the end effector aligns its inner axis along a trajectory, which can be determined according to the processing discussed above and/or according to the preoperative plan.

In Step 1004, the operator loads a tool (for example, a scalpel) with geometry that allows it to interface with the inner lumen into the proximal end of the end effector. The end effector has the ability to lock/engage the scalpel or to passively guide it along the predetermined trajectory and allow the user to move it linearly along the axis.

According to some embodiments, if it is locked/engaged by the end effector, the end effector the has the ability to advance it linearly along the axis into the skin to create the skin incision. In some embodiments, once incision has been made, the tool (e.g., scalpel) can be retracted and withdrawn out of the body. In some embodiments, once fully withdrawn, the scalpel can be unlocked and removed from the proximal end of the end effector.

In Step 1006, operator then loads a burr with geometry that allows it to interface with the inner lumen. In some embodiments, the burr can be locked, advanced, turned on, retracted turned off, and disengaged by the robot or the user. In some embodiments, the end effector has the ability to advance the tool linearly along the axis, but the robot simultaneously or otherwise has the ability to move that axis along a different trajectory as determined by the robot controller in order to remove bone as determined by the operative plan. In some embodiments, once bone removal is complete, the burr can be retracted and disengaged from the end effector and, and removed by the user out the proximal end of the end effector.

In Step 1008, the operator then loads a tap with mating geometry into the end effector. In some embodiments, the end effector has the ability to engage, advance, rotate, retract, and disengage the tap. In some embodiments, the tap can be advanced at a set linear speed and rotational speed until a force against the tap is sensed by the robot end effector or torque in the joint. From there, the tap can be advanced at a constant rate and the rotational speed is proportional to the axial force applied. In some embodiments, the robot can employ a control loop to maintain a constant axial force as it advances the tap.

In some embodiments, the tap can be rotated at a constant rate and advanced at a rate proportional to the force sensed. In some embodiments, the robot can employ a control feedback loop to maintain a constant force. In some embodiments, the tap can be withdrawn by simultaneously rotating and retracting the tool until it is completely withdrawn from the patient and is unlocked and removed through the proximal end of the end effector.

In some embodiments, a multi axis force sensor can be used in the end effector or on the tool that can determine biometric or proprioceptive data by sensing the vibrations and changes in vibration from the motor end effector. In some embodiments, the vibrations of the motor creates a movement profile at the end of the tool that can be sensed by an accelerometer placed on the end of the tool. In some embodiments, changes to the movement profile can be used to algorithmically determine forces on the tool. Forces such as, but not limited to, contact force can be sensed such the robot can sense if it is touching bony anatomy and verify that against the registration to determine if the registration is valid. The multi axis force sensor has the ability to replicate the feeling of touch that spine surgeons typically use when performing spine procedures.

In some embodiments, the multi axis force sensor can be used to sense forces while burring, drilling, tapping or screw a pedicle. These forces can be used to algorithmically determine the integrity of the bone, the quality of the screw purchase, the likely pullout strength of the bone, the likelihood or possibility that the screw trajectory exited bony anatomy, among other biometric data. In some embodiments, the force torque sensor on the robotic arm or in the end effector can be used to sense the forces used to interpret that data.

Without the use of navigation or robotics, common surgeon practice may be to use landmark check confirmation by placing the tip of the tool and confirming the relative pose and location of the tool tip to the vertebrae with a fluoroscopic image. In some embodiments, such workflow can be replicated by an autonomous robot as a validity check of the registered vertebral body pose or to reduce tool tip location error relative to the anatomy. In some embodiments, the robot has n arms (e.g., two arms) each with an end effector and tool attached. Each arm can bilaterally contact a vertebrae without disrupting its location in space utilizing the previously described multi axis force sensor or force torque sensor of the robotic arm. In some embodiments, with both tool tips at known locations as being tracked by the camera, a fluoroscopic image can be taken. In some embodiments, utilizing the auto-segmentation of the tool and the vertebrae in the image and keypoint detection to determine their pose relative to each other, the registration can be validated, invalidated, or refined.

In Step 1010, the operator then loads a screw and driver with mating geometry through the proximal end of the end effector. In some embodiments, the end effector inserts the screw in a manner similar to the tap. In some embodiments, once inserted, the robot can maintain engagement and therefore fixation to the spine, or it can disengage the driver from the screw and retract the driver through the proximal end of the end effector.

According to some embodiments, while maintaining fixation to the screw, Process 100 can be repeated on the contralateral side with the second robot arm. The fixation to the implanted screw maintain fidelity of the navigation, provides a counter torque for opposing side insertion, and enables the robot to aid in correction maneuvers.

Figure 12:
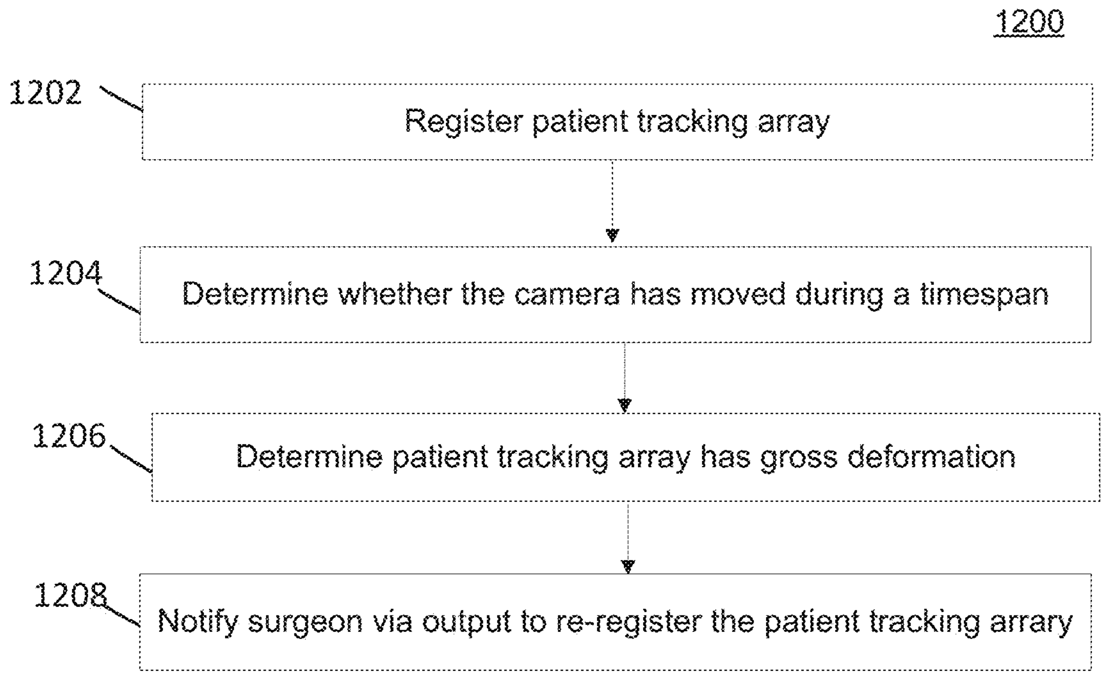
FIG. 12 illustrates an exemplary data flow according to some embodiments of the present disclosure.

Turning to FIG. 12, provided is Process 1200 which details non-limiting example embodiments for determining a tracking array shift from a camera element. In some embodiments, as discussed herein, the framework can determine a gross patient tracking array movement based on camera-centric tracking. In some embodiments, the framework can perform a re-registration of a patient tracking array after the gross movement determination as indicated from table-frame based redundant tracking array and/or camera-centric movement detection, as discussed herein.

According to some embodiments, Process 1200 begins with Step 1202 where a patient tracking array is registered. This can be performed in a similar manner as discussed above.

In Step 1204, engine 200 can determine whether a camera has moved during a timespan (or predetermined/dynamically determined time period). In some embodiments, the timespan can correspond to a predetermined time period, which can be in accordance with a time to register, time to perform a surgical step/procedure, time between captured images, and the like, or some combination thereof. In some embodiments, engine 200 can cause an IMU associated with a camera (e.g., imaging device 106, for example) to perform such analysis and determination.

In some embodiments, sensors on the imaging device 106 can be leveraged to determine if a threshold amount of movement have been detected (e.g., gyroscope, accelerometer, GPS, for example). In some embodiments, images captured at or around the time span can be compared, and if there is a difference in pixels (e.g., via computer vision, for example) beyond a threshold amount, then a movement can be detected.

In Step 1206, engine 200 can determine if the patient tracking array has a gross deformation. And, in Step 1208, upon the gross deformation determination, the surgeon can be notified via an output, which can be visibly displayed on the UI and/or audible output, in a similar manner as discussed above. Thus, according to some embodiments, if/when a patient tracking array gross deformation is observed based on camera-centric reference frame during a timespan in which no IMU signal indicates camera movement, a surgeon can be notified to re-register patient-based tracking array.

According to some embodiments, processing of Process 1200 can be utilized for re-registration of a patient tracking array from a table-frame based on redundant tracking array and/or detected camera-centric movements.

According to some embodiments, a patient tracking array can be registered (as discussed above, a 2D/3D merge and/or iCT, for example), whereby, in some embodiments, it can be merged concurrently with a redundant table-based tracking array.

In some embodiments, the table-based tracking array can be used to determine if there is gross deformation of patient-tracking array, with only one element of the table-based tracking array required to be visible at any point in time to determine relative movement of patient tracking array.

In some embodiments, additionally, camera movement can be determined based on reference to table-based tracking array. If no movement is detected, gross deformation of patient-tracking array can be detected via camera-frame based movement (e.g., based on a form acceptance criteria indicating the patient tracking array has moved along the tracking array tool axis).

In some embodiments, when patient-based tracking array gross deformation is observed, a surgeon is notified to re-register patient-based tracking array, as discussed above.

In some embodiments, engine 200 may utilize a Tactile Elastomer to re-register a vertebral body with pose initialization via an iterative closest point algorithm based on table-based tracking array.

Figure 13:
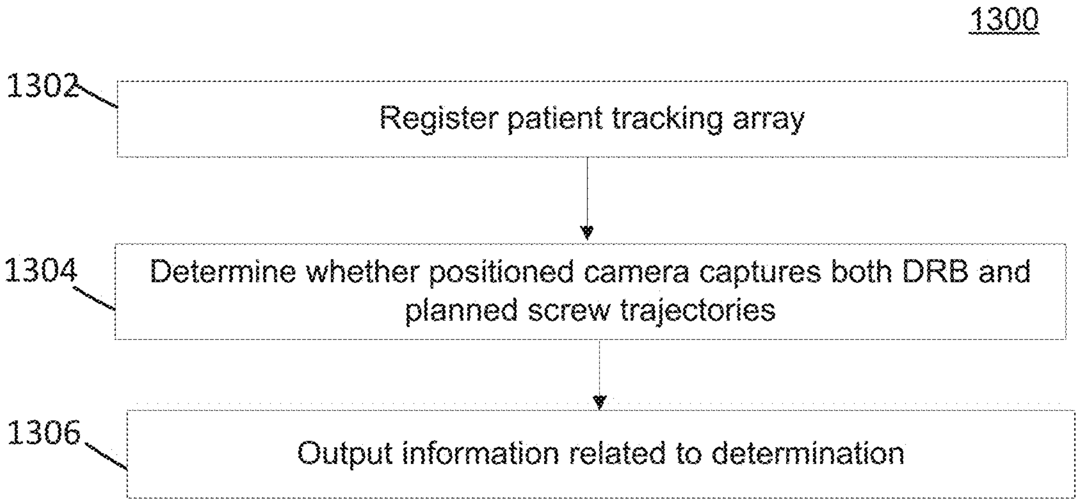
FIG. 13 illustrates an exemplary data flow according to some embodiments of the present disclosure.

In FIG. 13, Process 1300 provides non-limiting example embodiments for avoiding a line of sight obstruction during a spinal procedure (e.g., pedicle screw insertion/placement). In some embodiments, as discussed herein, engine 200 can operate to determine an optimal camera placement for simultaneously viewing a DRB and an instrument tracking array, which can be based on a pre-operative planned screw trajectory and/or intra-operative registration.

According to some embodiments, Process 1300 begins with Step 1302 where engine 200 can register a patient tracking array. As discussed above, this can be performed via the above processing via iCT and/or 2D/3D merge, among other mechanisms.

In Step 1304, engine 200 can determine whether the positioned camera captures both the DRB and the planned screw trajectories. According to some embodiments, engine 200 can execute a ML/AI algorithm, such as, for example, computer vision, neural network analysis, feature vector analysis, logistic regression, Hidden Markov Modelling, Bayes Theorem, and the like (in addition to any other algorithm discussed herein/above). Such ML/AI modelling can be executed based on a computational analysis of the preoperative planning, information related to screw trajectories (and/or angles), and determined camera position. As such, in some embodiments, engine 200 can parse data files that include information related to, but not limited to, preoperative plans, intra-operative procedures, an angle of incidence of the planned pedicle screw trajectory on surface topography, the surface topography, and/or any other information derivable that relates to any of the above Processes, spinal information, and the like, or some combination thereof. Such parsed information can be extracted, and fed to the ML/AI algorithms executed by engine 200 to perform the determination of Step 1304.

In Step 1306, engine 200 can compile, as an output, information related to the determination of Step 1304. In some embodiments, Step 1306 can involve communicating for display on the UI, for example, information related to whether the camera placement is capable of seeing (e.g., without obstruction) the navigated instruments throughout the entirety of the axial translation of the screw driver within the planned screw trajectories (e.g., each of the implantations and associated maneuvers for pedicle screw implantation, for example).

In some embodiments, the displayed output can provide suggested movements that can enable no obstruction, whereby such suggestions/recommendations can be compiled and displayed upon the determination that an obstruction exists (from Step 1306). In such embodiments, the recommendation can be compiled based on a computational, ML/AI analysis and determination as to a positioning of the camera(s) based on the trajectory of each screw.

According to some embodiments, the disclosed systems and methods can be provided as an overall system that interacts as a process as a whole, whereby Processes 300, 500, 700, 800, 1000, 1200 and 1300. Thus, according to some embodiments, the disclosed processing by engine 200, inclusive of its control and operation of Tactile Elastomer instrument and surgical robot (e.g., FIG. 9A) can involve preoperative planning and intraoperative procedures (and, ultimately, post-operative, whereby accuracy measures, among others, can be used to further train the modelling techniques utilized for each process).

By way of background, advanced surgical systems include many different types of equipment to assist the surgeon in performing surgical tasks, as discussed herein.

For example, medical visualization systems refer to visualization systems that are used for visualization and analysis of objects (preferably three-dimensional (3D) objects). Medical visualization systems include the selection of points at surfaces, selection of a region of interest, selection of objects. Medical visualization systems can be used for applications diagnosis, treatment planning, intraoperative support, documentation, educational purpose. Medical visualization systems can consist of microscopes, endoscopes/arthroscopes/laparoscopes, fiber optics, surgical lights, high-definition monitors, operating room cameras, and the like. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. According to some embodiments, medical visualization systems can be integrated and/or utilized via the disclosed framework, discussed supra.

X-ray can refer to a medical imaging instrument that uses X-ray radiation (e.g., X-ray range in the electromagnetic radiation spectrum) for the creation of images of the interior of the human body for diagnostic and treatment purposes. An X-ray instrument can also be referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube can be passed through a patient positioned to the detector. As the X-rays pass through the body, images may appear in shades of black and white, which may depend on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, operating console, collimator, grids, detector, radiographic film, and the like. According to some embodiments, an X-ray can be utilized via the disclosed framework, discussed supra.

MRI may refer to a medical imaging instrument that uses magnets for the creation of images of the interior of the human body for diagnostic and treatment purposes. Some of the applications where MRI may be used may be brain/spinal cord anomalies, tumors in the body, breast cancer screening, joint injuries, uterine/pelvic pain detection, heart problems. For the creation of the image by an MRI instrument, magnetic resonance may be produced by magnets that produce a magnetic field that induces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field, and energy release may be dependent on environmental factors and the chemical nature of the molecules. MRI may be suitable for imaging of non-bony parts or soft tissues of the body. MRI may be less harmful as it does not use damaging ionizing radiation as in the X-ray instrument. MRI instrument may consist of magnets, gradients, radiofrequency system, computer control system. Some areas where imaging by MRI should be prohibited may be people with implants. According to some embodiments, MRI can be utilized via the disclosed framework, discussed supra.

CT may refer to a medical imaging instrument that uses an X-ray radiation (e.g., X-ray range in the electromagnetic radiation spectrum) for the creation of, for example, cross-sectional images of the interior of the human body for diagnostic and treatment purposes. CT may be a computerized x-ray imaging procedure in which a narrow beam of x-rays is aimed at a patient and quickly rotated around the body, producing signals that are processed by the machine's computer to generate cross-sectional images—or "slices"—of the body The CT instrument may produce cross-sectional images of the body. Computed tomography instrument may be different from an X-ray instrument as it creates 3-dimensional cross-sectional images of the body while X-ray creates 2-dimensional images of the body. In such a case, the 3-dimensional cross-sectional images may be created by taking images from different angles, which may be done by taking a series of tomographic images from different angles. The different taken images may be collected by a computer and digitally stacked to form a three-dimensional image of the patient. For creation of images by the CT instrument, for example, a CT scanner may use a motorized x-ray source that rotates around the circular opening of a donut-shaped structure called a gantry while the x-ray tube rotates around the patient shooting narrow beams of x-rays through the body. Some of the applications where CT may be used may be blood clots, bone fractures, including subtle fractures not visible on X-ray, organ injuries. According to some embodiments, CT can be utilized via the disclosed framework, discussed supra.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis/treatment/guidance during medical procedures e.g., biopsies, internal organs such as liver/kidneys/pancreas, fetal monitoring, and the like, in soft tissues, muscles, blood vessels, tendons, joints. Ultrasound may be used for internal (transducer is placed in organs e.g., vagina) and external (transducer is placed on chest for heart monitoring or abdomen for the fetus). An ultrasound machine may consist of a monitor, keyboard, processor, data storage, probe, and transducer. According to some embodiments, an ultrasound can be utilized via the disclosed framework, discussed supra.

According to some embodiments, equipment refers to a set of articles, tools, or objects which help to implement or achieve an operation or activity. A medical equipment (or medical imaging equipment) refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, and the like. The medical equipment works by taking a signal from a measurand/patient, a transducer for converting one form of energy to electrical energy, signal conditioner such as an amplifier, filters, and the like, to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. According to some embodiments, medical equipment can be utilized via the disclosed framework, discussed supra.

Robotic systems refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, and the like. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into surgical robotic systems, rehabilitative robotic systems, non-invasive radiosurgery robots, hospital & pharmacy robotic systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally invasive procedures. The systems include computer-controlled electromechanical devices that work in response to controls manipulated by the surgeons. According to some embodiments, robotic systems can be utilized via the disclosed framework, discussed supra.

Figure 14:
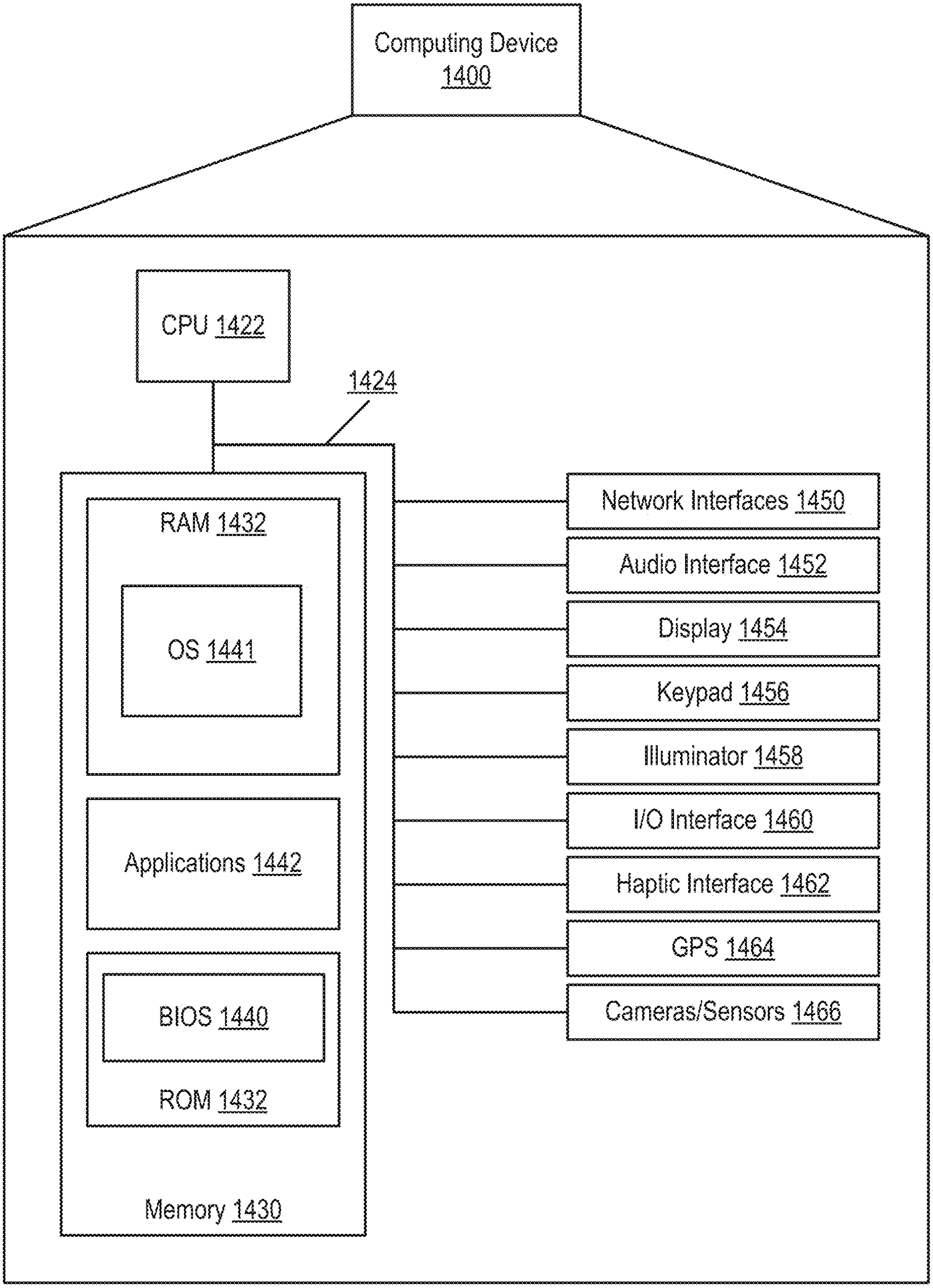
FIG. 14 is a block diagram illustrating a computing device showing an example of a client or server device used in various embodiments of the present disclosure.

FIG. 14 is a schematic diagram illustrating a client device showing an example embodiment of a client device that may be used within the present disclosure. Client device 1400 may include many more or less components than those shown in FIG. 14. However, the components shown are sufficient to disclose an illustrative embodiment for implementing the present disclosure. Client device 1400 may represent, for example, UE 102 discussed above at least in relation to FIG. 1.

As shown in the figure, in some embodiments, Client device 1400 includes a processing unit (CPU) 1422 in communication with a mass memory 1430 via a bus 1424. Client device 1400 also includes a power supply 1426, one or more network interfaces 1450, an audio interface 1452, a display 1454, a keypad 1456, an illuminator 1458, an input/output interface 1460, a haptic interface 1462, an optional global positioning systems (GPS) receiver 1464 and a camera(s) or other optical, thermal or electromagnetic sensors 1466. Device 1400 can include one camera/sensor 1466, or a plurality of cameras/sensors 1466, as understood by those of skill in the art. Power supply 1426 provides power to Client device 1400.

Client device 1400 may optionally communicate with a base station (not shown), or directly with another computing device. In some embodiments, network interface 1450 is sometimes known as a transceiver, transceiving device, or network interface card (NIC).

Audio interface 1452 is arranged to produce and receive audio signals such as the sound of a human voice in some embodiments. Display 1454 may be a liquid crystal display (LCD), gas plasma, light emitting diode (LED), or any other type of display used with a computing device. Display 1454 may also include a touch sensitive screen arranged to receive input from an object such as a stylus or a digit from a human hand.

Keypad 1456 may include any input device arranged to receive input from a user. Illuminator 1458 may provide a status indication and/or provide light.

Client device 1400 also includes input/output interface 1460 for communicating with external. Input/output interface 1460 can utilize one or more communication technologies, such as USB, infrared, Bluetooth™, or the like in some embodiments. Haptic interface 1462 is arranged to provide tactile feedback to a user of the client device.

Optional GPS transceiver 1464 can determine the physical coordinates of Client device 1400 on the surface of the Earth, which typically outputs a location as latitude and longitude values. GPS transceiver 1464 can also employ other geo-positioning mechanisms, including, but not limited to, triangulation, assisted GPS (AGPS), E-OTD, CI, SAI, ETA, BSS or the like, to further determine the physical location of client device 1400 on the surface of the Earth. In one embodiment, however, Client device may through other components, provide other information that may be employed to determine a physical location of the device, including for example, a MAC address, Internet Protocol (IP) address, or the like.

Mass memory 1430 includes a RAM 1432, a ROM 1434, and other storage means. Mass memory 1430 illustrates another example of computer storage media for storage of information such as computer readable instructions, data structures, program modules or other data. Mass memory 1430 stores a basic input/output system ("BIOS") 1440 for controlling low-level operation of Client device 1400. The mass memory also stores an operating system 1441 for controlling the operation of Client device 1400.

Memory 1430 further includes one or more data stores, which can be utilized by Client device 1400 to store, among other things, applications 1442 and/or other information or data. For example, data stores may be employed to store information that describes various capabilities of Client device 1400. The information may then be provided to another device based on any of a variety of events, including being sent as part of a header (e.g., index file of the HLS stream) during a communication, sent upon request, or the like. At least a portion of the capability information may also be stored on a disk drive or other storage medium (not shown) within Client device 1400.

Applications 1442 may include computer executable instructions which, when executed by Client device 1400, transmit, receive, and/or otherwise process audio, video, images, and enable telecommunication with a server and/or another user of another client device. Applications 1442 may further include a client that is configured to send, to receive, and/or to otherwise process gaming, goods/services and/or other forms of data, messages and content hosted and provided by the platform associated with engine 200 and its affiliates.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, and the like).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium for execution by a processor. Modules may be integral to one or more servers, or be loaded and executed by one or more servers. One or more modules may be grouped into an engine or an application.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores," may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, and the like).

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

For the purposes of this disclosure the term "user," "subscriber" "consumer" or "customer" should be understood to refer to a user of an application or applications as described herein and/or a consumer of data supplied by a data provider. By way of example, and not limitation, the term "user" or "subscriber" can refer to a person who receives data provided by the data or service provider over the Internet in a browser session, or can refer to an automated software application which receives the data and stores or processes the data. Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

What is claimed is:

1. A method comprising;

identifying, by a device, a medical image of a patient;

analyzing, by the device, medical image, the analysis comprising auto-segmentation of the medical image;

determining, by the device, based on the analysis, an optimal location for surface-based registration;

performing, by the device, registration of a patient tracking array;

determining, by the device, an accuracy of pedicle screw placement;

creating, by the device, a vertebral body specific registration; and outputting, by the device, tracking information based at least on the created vertebral body specific registration and/or patient tracking array, the output caused to be displayed within a user interface (UI).

2. The method of claim 1, further comprising:

creating, based on the patient tracking array, a surface topography;

determining a set of points associated with a set of touchpoints;

navigating the set of points within a navigational space;

determining, based on the navigation, a registration accuracy; and determining and outputting an indication to re-register or proceed based on the registration accuracy.

3. The method of claim 1, further comprising:

determining, based on the auto-segmentation of the medical image, information related to a planned pedicle screw implantation;

determining skive probability based on an applied skive model;

determining, based on the skive probability, an optimal pilot hole; and outputting, for displaying within the UI, information related to the optimal pilot hole.

4. The method of claim 1, further comprising:

determining, based at least in part on the patient tracking array, whether a camera has moved during a timespan;

determining that the patient tracking array has a gross deformation; and outputting, via the UI, a notification indicating a need to re-register the patient tracking array.

5. The method of claim 1, further comprising:

determining, based at least in part on the patient tracking array, whether a camera positioned captures both dynamic reference base (DRB) and planned screw trajectories; and outputting, via the UI, information related to the determination of the camera positioning, wherein when both the DRB and planned screw trajectories are captured, a proceed message is provided, wherein when both are not captured, a repositioning message is provided.

6. The method of claim 1, further comprising:

determining a dynamic re-registration and reconfiguration (DRR) simulation, the DDR simulation corresponding to a theoretical fluoroscopic image based on the instantaneous pose of a C-arm of the device and the patient relative to one another at any point in time after an initial registration; and outputting to a user interface (UI) the DDR simulation.

7. A non-transitory computer-readable storage medium tangibly encoded with computer-executable instructions, that when executed by a device, perform a method comprising:

identifying, by a device, a medical image of a patient;

analyzing, by the device, medical image, the analysis comprising auto-segmentation of the medical image;

determining, by the device, based on the analysis, an optimal location for surface-based registration;

performing, by the device, registration of a patient tracking array;

determining, by the device, an accuracy of pedicle screw placement;

creating, by the device, a vertebral body specific registration; and outputting, by the device, tracking information based at least on the created vertebral body specific registration and/or patient tracking array, the output caused to be displayed within a user interface (UI).

8. The non-transitory computer-readable storage medium of claim 7, further comprising:

creating, based on the patient tracking array, a surface topography;

determining a set of points associated with a set of touchpoints;

navigating the set of points within a navigational space;

determining, based on the navigation, a registration accuracy; and determining and outputting an indication to re-register or proceed based on the registration accuracy.

9. The non-transitory computer-readable storage medium of claim 7, further comprising:

determining, based on the auto-segmentation of the medical image, information related to a planned pedicle screw implantation;

determining skive probability based on an applied skive model;

determining, based on the skive probability, an optimal pilot hole; and outputting, for displaying within the UI, information related to the optimal pilot hole.

10. The non-transitory computer-readable storage medium of claim 7, further comprising:

determining, based at least in part on the patient tracking array, whether a camera has moved during a timespan;

determining that the patient tracking array has a gross deformation; and outputting, via the UI, a notification indicating a need to re-register the patient tracking array.

11. The non-transitory computer-readable storage medium of claim 7, further comprising:

determining, based at least in part on the patient tracking array, whether a camera positioned captures both dynamic reference base (DRB) and planned screw trajectories; and outputting, via the UI, information related to the determination of the camera positioning, wherein when both the DRB and planned screw trajectories are captured, a proceed message is provided, wherein when both are not captured, a repositioning message is provided.

12. The non-transitory computer-readable storage medium of claim 7, further comprising:

determining a dynamic re-registration and reconfiguration (DRR) simulation, the DDR simulation corresponding to a theoretical fluoroscopic image based on the instantaneous pose of a C-arm of the device and the patient relative to one another at any point in time after an initial registration; and outputting to a user interface (UI) the DDR simulation.

* * * * *